US008945217B2

(12) United States Patent
Savage et al.

(10) Patent No.: US 8,945,217 B2
(45) Date of Patent: Feb. 3, 2015

(54) MEDICAL DEVICES INCORPORATING CERAGENIN-CONTAINING COMPOSITES

(75) Inventors: Paul B. Savage, Mapleton, UT (US); Roy D. Bloebaum, Salt Lake City, UT (US); Dustin L. Williams, Bountiful, UT (US); Kristofer D. Sinclair, Salt Lake City, UT (US); Bryan S. Haymond, Salt Lake City, UT (US)

(73) Assignees: Brigham Young University, Provo, UT (US); University of Utah Research Foundation, Salt Lake City, UT (US)

( * ) Notice: Subject to any disclaimer, the term of this patent is extended or adjusted under 35 U.S.C. 154(b) by 115 days.

(21) Appl. No.: 13/594,612

(22) Filed: Aug. 24, 2012

(65) Prior Publication Data

US 2013/0245760 A1  Sep. 19, 2013

Related U.S. Application Data

(60) Provisional application No. 61/575,646, filed on Aug. 25, 2011, provisional application No. 61/576,903, filed on Dec. 16, 2011, provisional application No. 61/576,905, filed on Dec. 16, 2011.

(51) Int. Cl.
*A61F 2/02* (2006.01)
*A01N 45/00* (2006.01)
(Continued)

(52) U.S. Cl.
CPC ............... *A01N 45/00* (2013.01); *A01N 25/10* (2013.01); *A61F 2/02* (2013.01); *A61L 27/34* (2013.01); *A61L 27/54* (2013.01); *A61L 2300/404* (2013.01)
USPC ...................................... 623/11.11

(58) Field of Classification Search
USPC ...................................... 623/11.11
See application file for complete search history.

(56) References Cited

U.S. PATENT DOCUMENTS

| 4,972,848 A | 11/1990 | Di Domenico |
| 6,228,393 B1 | 5/2001 | DiCosmo et al. |

(Continued)

FOREIGN PATENT DOCUMENTS

| WO | WO 9524415 | 9/1995 |
| WO | WO 9944616 | 9/1999 |

(Continued)

OTHER PUBLICATIONS

Emily L. Perry et al. "Assessing peri-implant tissue infection prevention in a percutaneous model" Journal of Biomedical Materials Research Part B: Applied Biomaterials, vol. 92B, Nov. 19, 2009, pp. 397-408.

(Continued)

*Primary Examiner* — Randy Shay
*Assistant Examiner* — Dinah Baria
(74) *Attorney, Agent, or Firm* — Workman Nydegger

(57) ABSTRACT

A medical device that includes a coating of a composite material that includes a polymeric material having a void structure and particulate ceragenin material (i.e., ceragenin particles) associated with the void structure. The average particle size of the ceragenin particles in the composite is in a range from 5 nm to 20 μm, 50 nm to 10 μm, 100 nm to 5 Ξm, or 1 μm to 10 μm. The composite has a high loading of ceragenin particles (e.g., about 10% to about 25%, by weight). The composite has good polymer stability, the ability to release ceragenins from the ceragenin particles disposed in the composite over a sustained period of time at a characteristic elution rate, and the ability to kill large numbers of bacteria and other susceptible microbes over the sustained period of time.

21 Claims, 17 Drawing Sheets

(51) Int. Cl.
*A01N 25/10* (2006.01)
*A61L 27/34* (2006.01)
*A61L 27/54* (2006.01)

(56) References Cited

U.S. PATENT DOCUMENTS

| | | |
|---|---|---|
| 6,350,738 B1 | 2/2002 | Savage et al. |
| 6,486,148 B2 | 11/2002 | Savage et al. |
| 6,767,904 B2 | 7/2004 | Savage et al. |
| 6,939,376 B2 * | 9/2005 | Shulze et al. ........ 623/1.42 |
| 7,282,214 B2 | 10/2007 | Wilcox et al. |
| 7,598,234 B2 | 10/2009 | Savage et al. |
| 7,754,705 B2 | 7/2010 | Savage et al. |
| 8,211,879 B2 | 7/2012 | Savage et al. |
| 8,529,681 B1 | 9/2013 | Hibbs et al. |
| 8,623,416 B2 | 1/2014 | Zasloff et al. |
| 8,784,857 B2 | 7/2014 | Savage |
| 2004/0009227 A1 | 1/2004 | Yao |
| 2005/0032765 A1 | 2/2005 | Savage et al. |
| 2005/0075321 A1 | 4/2005 | Ahlem et al. |
| 2005/0244468 A1 * | 11/2005 | Huang et al. ............... 424/427 |
| 2006/0269485 A1 | 11/2006 | Friedman et al. |
| 2007/0106393 A1 * | 5/2007 | Miles et al. ............... 623/23.5 |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0174035 A1 | 7/2008 | Winterton |
| 2008/0188819 A1 | 8/2008 | Kloke et al. |
| 2010/0330086 A1 | 12/2010 | Savage et al. |
| 2011/0123624 A1 | 5/2011 | Zasloff |
| 2012/0088733 A1 | 4/2012 | Kim et al. |
| 2013/0022651 A1 | 1/2013 | Savage |
| 2013/0053507 A1 | 2/2013 | Savage |
| 2013/0243823 A1 | 9/2013 | Genberg et al. |
| 2013/0243840 A1 | 9/2013 | Savage et al. |

FOREIGN PATENT DOCUMENTS

| | | |
|---|---|---|
| WO | WO 0042058 | 7/2000 |
| WO | WO 0214342 | 2/2002 |
| WO | WO 03015757 | 2/2003 |
| WO | WO 2007089903 | 8/2007 |
| WO | WO 2007089906 | 8/2007 |
| WO | WO 2007089907 | 8/2007 |
| WO | WO 2009079066 | 6/2009 |
| WO | WO 2010036427 | 4/2010 |
| WO | WO 2011109704 | 9/2011 |
| WO | WO 2012061651 | 5/2012 |
| WO | WO2013/109236 | 7/2013 |

OTHER PUBLICATIONS

Savage et al.: "Antibacterial Activities of Thin Films Containing Ceragenins", Microbial Surfaces: Structure, Interactions and Reactivity, ACS, May 30, 2008, pp. 65-78.

P. B Savage et al.: "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.

P.B. Savage et al.: "Thin Films Containing Ceragenins Prevent Biofilm Formation on Endotracheal Tubes", 9th International Federation of Infection Control Congress, Oct. 14, 2008, pp. 1-1.

U.S. Appl. No. 14/288,126, filed May 27, 2014, Savage, et al.

Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.

K.D. Sinclair, et al., "Development of a broad spectrum polymer-released antimicrobial coating for the prevention of resistant strain bacterial infections", Journal of Biomedical Materials Research Part A., vol. 100A, No. 10, May 24, 2012, pp. 2732-2738.

Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.

K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.

Isogai E et al: "Ceragenin CSA-13 exhibits antimicrobial activity against cariogenic and periodontopathic bacteria", Oral Microbiology and Immunology, vol. 24, No. 2, Apr. 2009, pp. 170-172.

Van Bambeke et al: "The bacterial envelope as a target for novel anti-MRSA antibiotics", Trends in Pharmacological Sciences, Elsevier, Haywarth, GB, vol. 29, No. 3, Feb. 11, 2008, pp. 124-134.

Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000, pp. 2837-2840.

Alhanout K et al: "Squalamine as an example of a new potent antimicrobial agents class: a critical review", Current Medicinal Chemistry 2010, vol. 17, No. 32, 2010, pp. 3909-3917.

International Search Report for PCT Application No. PCT/US2012/047750, Mailed Date: Oct. 5, 2012, Filed Date: Sep. 27, 2012, 3 pages.

Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.

U.S. Appl. No. 13/554,957, Apr. 1, 2014, Office Action.
U.S. Appl. No. 13/554,957, Aug. 1, 2014, Notice of Allowance.
U.S. Appl. No. 13/594,608, Jan. 30, 2014, Office Action.
U.S. Appl. No. 13/615,324, Jan. 30, 2014, Office Action.
U.S. Appl. No. 13/554,930, Jul. 11, 2014, Office Action.

* cited by examiner

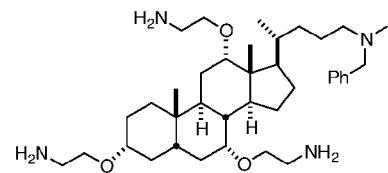

CSA-1 Chemical Formula: $C_{38}H_{66}N_4O_3$
Exact Mass: 626.5135
Molecular Weight: 626.9556

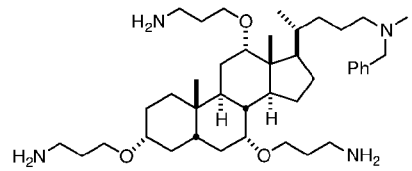

CSA-2 Chemical Formula: $C_{41}H_{72}N_4O_3$
Exact Mass: 668.5604
Molecular Weight: 669.0354

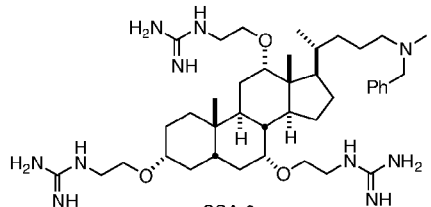

CSA-3
Chemical Formula: $C_{41}H_{72}N_{10}O_3$
Exact Mass: 752.5789
Molecular Weight: 753.0756

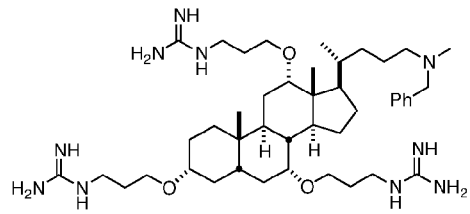

CSA-4 Chemical Formula: $C_{44}H_{78}N_{10}O_3$
Exact Mass: 794.6258
Molecular Weight: 795.1553

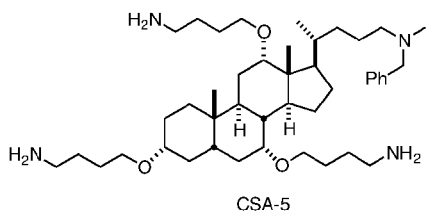

CSA-5
Chemical Formula: $C_{41}H_{79}N_3O_4$
Exact Mass: 677.6071
Molecular Weight: 678.0837

Chemical Formula: $C_{44}H_{78}N_4O_3$
Exact Mass: 710.6074
Molecular Weight: 711.1151

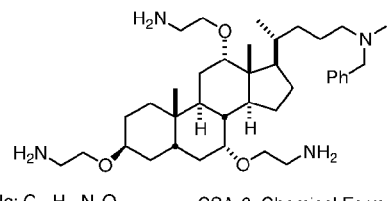

CSA-6 Chemical Formula: $C_{38}H_{66}N_4O_3$
Exact Mass: 626.5135
Molecular Weight: 626.9556

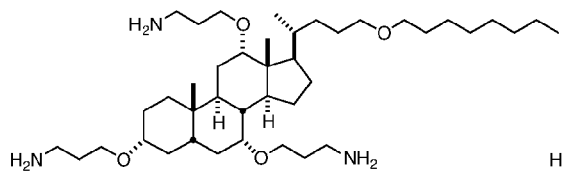

CSA-7 Chemical Formula: $C_{33}H_{63}N_3O_4$
Exact Mass: 565.4819
Molecular Weight: 565.8710

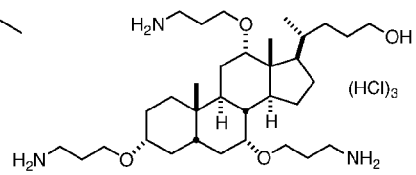

CSA-8
Chemical Formula: $C_{33}H_{66}Cl_3N_3O_4$
Exact Mass: 673.4119
Molecular Weight: 675.2538

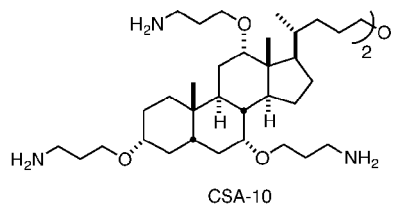

CSA-10

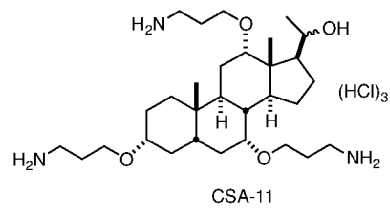

CSA-11

Chemical Formula: $C_{30}H_{60}Cl_3N_3O_4$
Exact Mass: 631.3649
Molecular Weight: 633.1741

*FIG. 1*

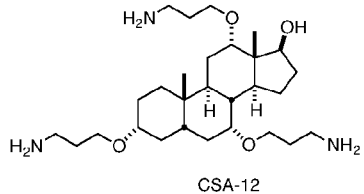

CSA-12
Chemical Formula: $C_{28}H_{53}N_3O_4$
Exact Mass: 495.4036
Molecular Weight: 495.7381

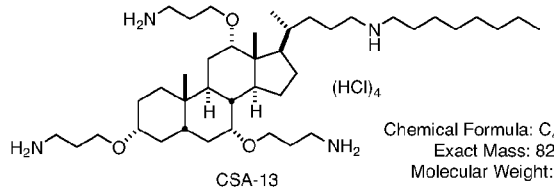

CSA-13
Chemical Formula: $C_{41}H_{80}N_4O_3$
Exact Mass: 676.6230
Molecular Weight: 677.0989

(HCl)$_4$
Chemical Formula: $C_{41}H_{84}Cl_4N_4O_3$
Exact Mass: 820.5298
Molecular Weight: 822.9427

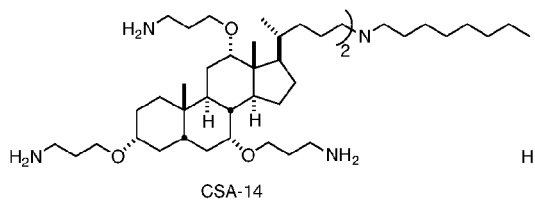

CSA-14
Chemical Formula: $C_{34}H_{65}N_3O_4$
Exact Mass: 579.4975
Molecular Weight: 579.8976

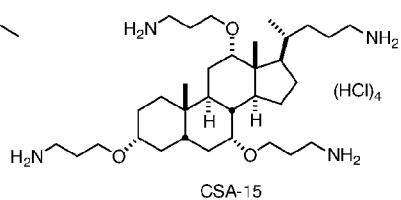

CSA-15
(HCl)$_4$
Chemical Formula: $C_{33}H_{68}Cl_4N_4O_3$
Exact Mass: 708.4046
Molecular Weight: 710.7300

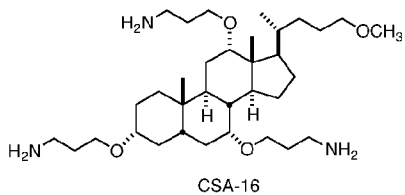

CSA-16
Chemical Formula: $C_{36}H_{73}N_3O_4$
Exact Mass: 635.56
Molecular Weight: 636

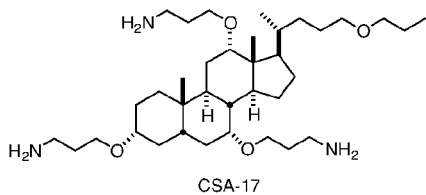

CSA-17
Chemical Formula: $C_{38}H_{73}N_3O_4$
Exact Mass: 635.5601
Molecular Weight: 636.0039

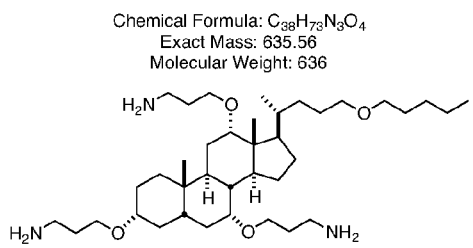

CSA-18 Chemical Formula: $C_{38}H_{73}N_3O_4$
Exact Mass: 635.5601
Molecular Weight: 636.0039

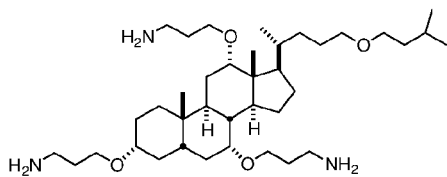

CSA-19
Chemical Formula: $C_{33}H_{63}N_3O_7S$
Exact Mass: 645.44
Molecular Weight: 645.93

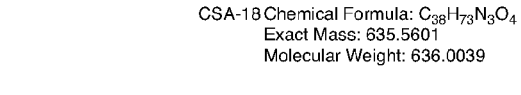

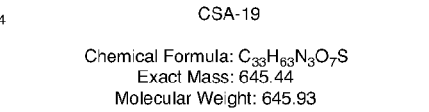

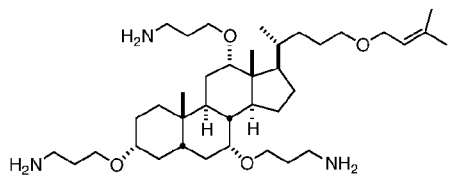

CSA-20 Chemical Formula: $C_{38}H_{71}N_3O_4$
Exact Mass: 633.5445
Molecular Weight: 633.9880

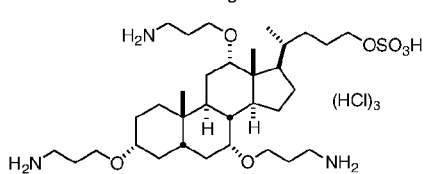

CSA-21
(HCl)$_3$
Chemical Formula: $C_{33}H_{66}Cl_3N_3O_7S$
Exact Mass: 753.3687
Molecular Weight: 755.3170

FIG. 1 (Continued)

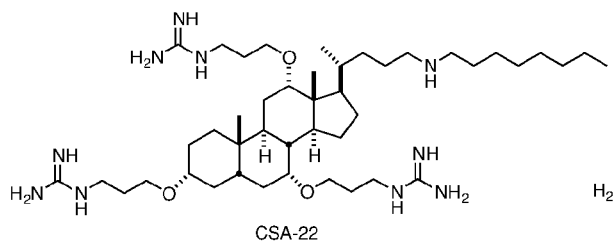

Chemical Formula: C$_{44}$H$_{86}$N$_{10}$O$_3$
Exact Mass: 802.6884
Molecular Weight: 803.2188

CSA-22

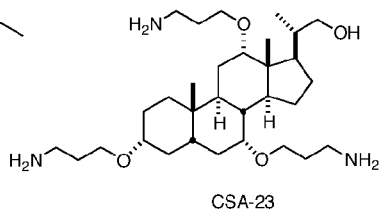

Chemical Formula: C$_{31}$H$_{59}$N$_3$O$_4$
Exact Mass: 537.4506
Molecular Weight: 537.8179

CSA-23

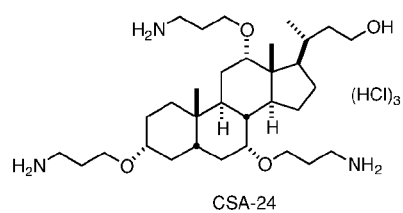

CSA-24
Chemical Formula: C$_{32}$H$_{64}$Cl$_3$N$_3$O$_4$
Exact Mass: 659.3962
Molecular Weight: 661.2273

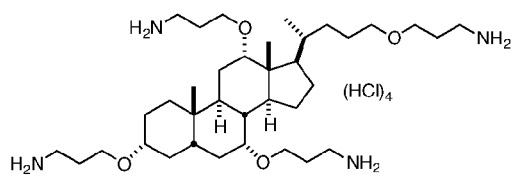

Chemical Formula: C$_{36}$H$_{70}$N$_4$O$_4$
Exact Mass: 622.54
Molecular Weight: 622.97

CSA-25
Chemical Formula: C$_{36}$H$_{74}$Cl$_4$N$_4$O$_4$
Exact Mass: 766.4464
Molecular Weight: 768.8092

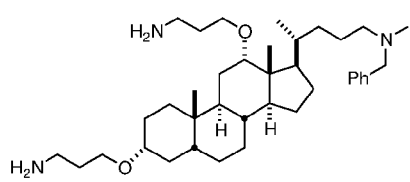

CSA-26 Chemical Formula: C$_{38}$H$_{65}$N$_3$O$_2$
Exact Mass: 595.5077
Molecular Weight: 595.9416

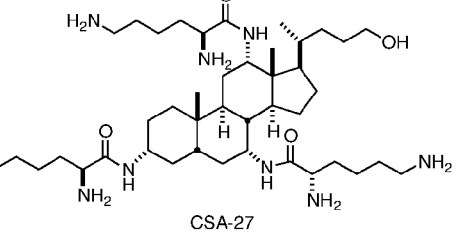

CSA-27

Chemical Formula: C$_{24}$H$_{45}$N$_3$O
Exact Mass: 391.3563
Molecular Weight: 391.6336

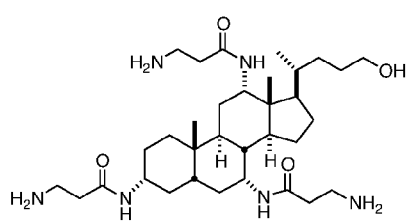

CSA-28
Chemical Formula: C$_{33}$H$_{60}$N$_6$O$_4$
Exact Mass: 604.4676
Molecular Weight: 604.8673

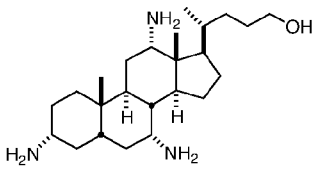

CSA-29

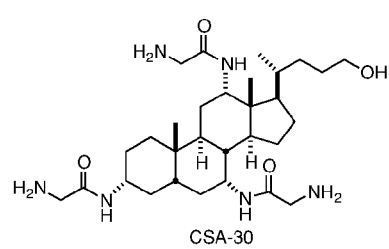

CSA-30

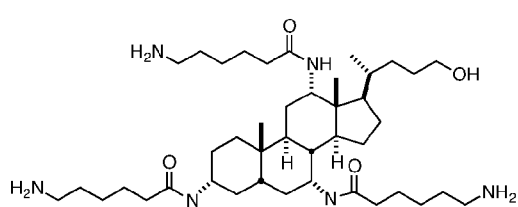

Chemical Formula: C$_{30}$H$_{54}$N$_6$O$_4$
Exact Mass: 562.4207
Molecular Weight: 562.7876

CSA-31 Chemical Formula: C$_{42}$H$_{78}$N$_6$O$_4$
Exact Mass: 730.6085
Molecular Weight: 731.1065

FIG. 1 (Continued)

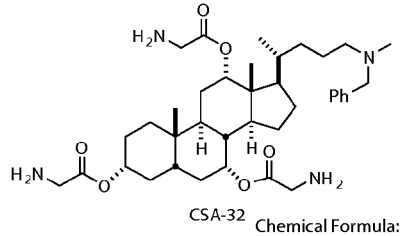

Chemical Formula: $C_{38}H_{60}N_4O_6$
Exact Mass: 668.4513
Molecular Weight: 668.9062

CSA-32

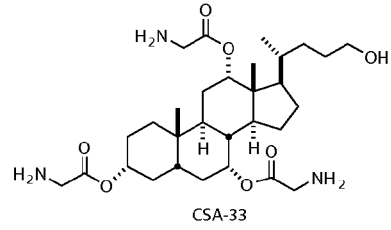

Chemical Formula: $C_{30}H_{51}N_3O_7$
Exact Mass: 565.3727
Molecular Weight: 565.7418

CSA-33

Chemical Formula: $C_{41}H_{66}N_4O_6$
Exact Mass: 710.4982
Molecular Weight: 710.9859

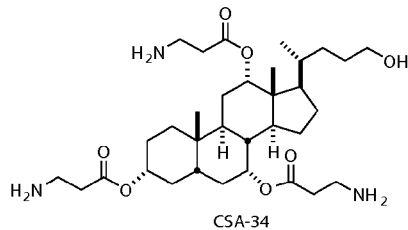

CSA-34

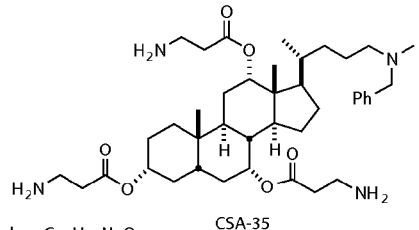

CSA-35

Chemical Formula: $C_{33}H_{57}N_3O_7$
Exact Mass: 607.4197
Molecular Weight: 607.8216

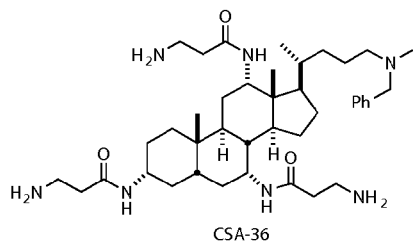

CSA-36

Chemical Formula: $C_{38}H_{74}N_4O_3$
Exact Mass: 634.5761
Molecular Weight: 635.0192

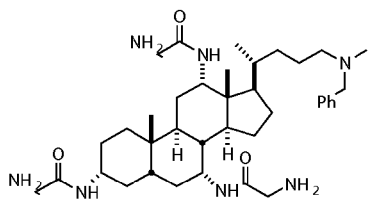

Chemical Formula: $C_{41}H_{69}N_7O_3$
Exact Mass: 707.5462
Molecular Weight: 708.0317

CSA-37 Chemical Formula: $C_{38}H_{63}N_7O_3$
Exact Mass: 665.4992
Molecular Weight: 665.9519

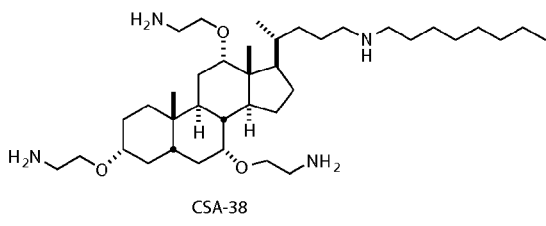

CSA-38

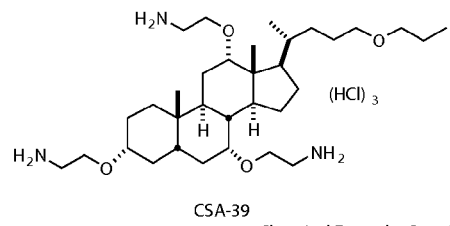

(HCl)$_3$

CSA-39

Chemical Formula: $C_{30}H_{57}N_3O_4$
Exact Mass: 523.4349
Molecular Weight: 523.7913

Chemical Formula: $C_{33}H_{66}Cl_3N_3O_4$
Exact Mass: 673.4119
Molecular Weight: 675.2538

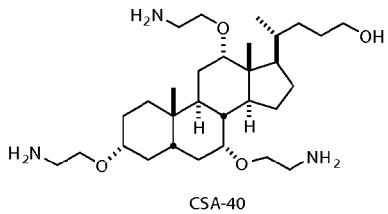

CSA-40

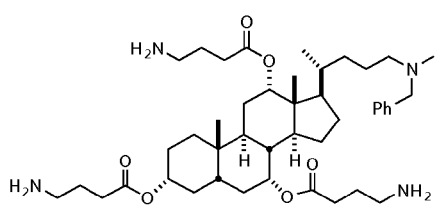

CSA-41 Chemical Formula: $C_{44}H_{72}N_4O_6$
Exact Mass: 752.5452
Molecular Weight: 753.0657

FIG. 1 (Continued)

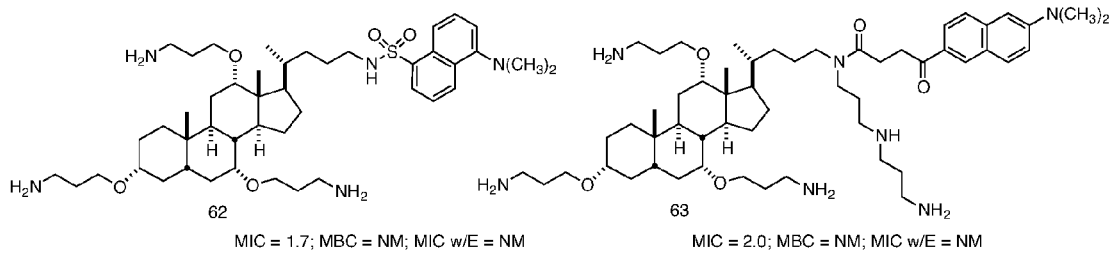

MIC = 1.7; MBC = NM; MIC w/E = NM    MIC = 2.0; MBC = NM; MIC w/E = NM

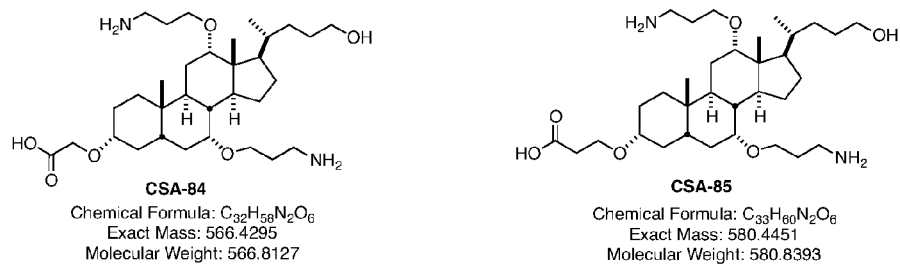

CSA-84
Chemical Formula: $C_{32}H_{58}N_2O_6$
Exact Mass: 566.4295
Molecular Weight: 566.8127

CSA-85
Chemical Formula: $C_{33}H_{60}N_2O_6$
Exact Mass: 580.4451
Molecular Weight: 580.8393

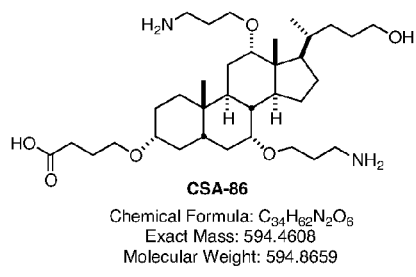

CSA-86
Chemical Formula: $C_{34}H_{62}N_2O_6$
Exact Mass: 594.4608
Molecular Weight: 594.8659

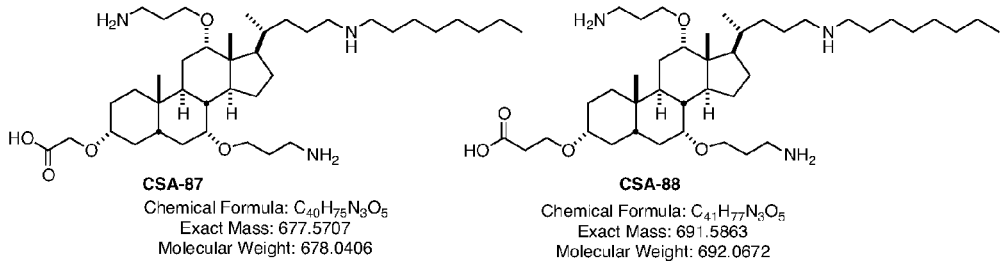

CSA-87
Chemical Formula: $C_{40}H_{75}N_3O_5$
Exact Mass: 677.5707
Molecular Weight: 678.0406

CSA-88
Chemical Formula: $C_{41}H_{77}N_3O_5$
Exact Mass: 691.5863
Molecular Weight: 692.0672

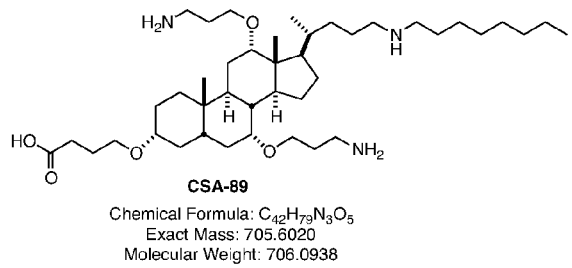

CSA-89
Chemical Formula: $C_{42}H_{79}N_3O_5$
Exact Mass: 705.6020
Molecular Weight: 706.0938

*FIG. 1 (Continued)*

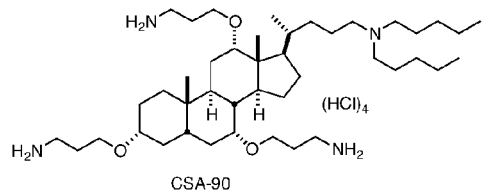

CSA-90
Chemical Formula: $C_{43}H_{88}Cl_4N_4O_3$
Exact Mass: 848.5611
Molecular Weight: 850.9958

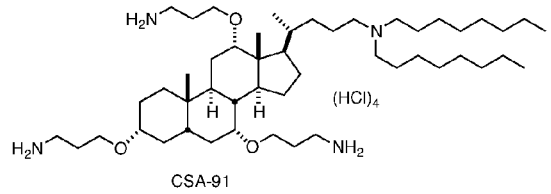

CSA-91
Chemical Formula: $C_{49}H_{100}Cl_4N_4O_6$
Exact Mass: 932.6550
Molecular Weight: 935.1553

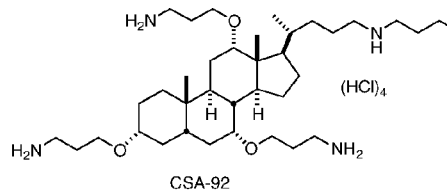

CSA-92
Chemical Formula: $C_{49}H_{100}Cl_4N_4O_3$
Exact Mass: 932.6550
Molecular Weight: 935.1553

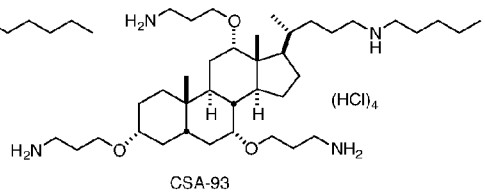

CSA-93
Chemical Formula: $C_{38}H_{78}Cl_4N_4O_3$
Exact Mass: 778.4828
Molecular Weight: 780.8629

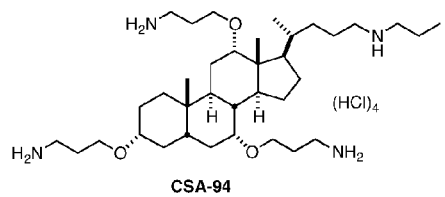

CSA-94
Chemical Formula: $C_{39}H_{74}Cl_4N_4O_3$
Exact Mass: 750.4515
Molecular Weight: 752.8098

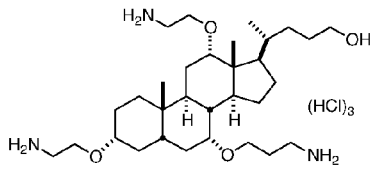

CSA-95
Chemical Formula: $C_{31}H_{62}Cl_3N_3O_4$
Exact Mass: 645.3806
Molecular Weight: 647.2007

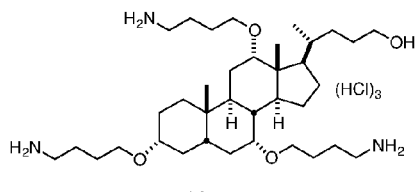

CSA-96
Chemical Formula: $C_{36}H_{72}Cl_3N_3O_4$
Exact Mass: 715.4588
Molecular Weight: 717.3336

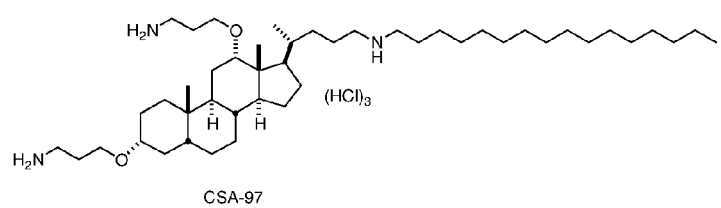

CSA-97
Chemical Formula: $C_{46}H_{92}Cl_3N_3O_2$
Exact Mass: 823.6255
Molecular Weight: 825.6006

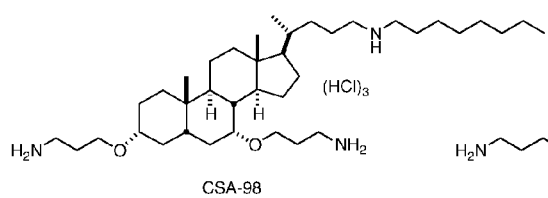

CSA-98
Chemical Formula: $C_{38}H_{76}Cl_3N_3O_2$
Exact Mass: 711.5003
Molecular Weight: 713.3879

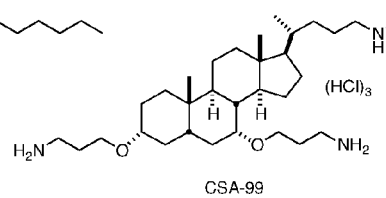

CSA-99
Chemical Formula: $C_{46}H_{92}Cl_3N_3O_2$
Exact Mass: 823.6255
Molecular Weight: 825.6006

*FIG. 1 (Continued)*

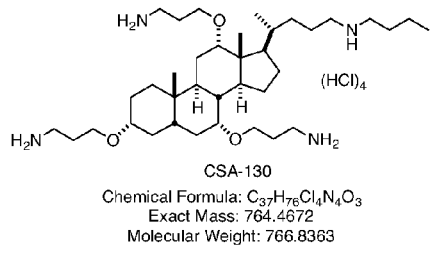

CSA-130
Chemical Formula: C₃₇H₇₆Cl₄N₄O₃
Exact Mass: 764.4672
Molecular Weight: 766.8363

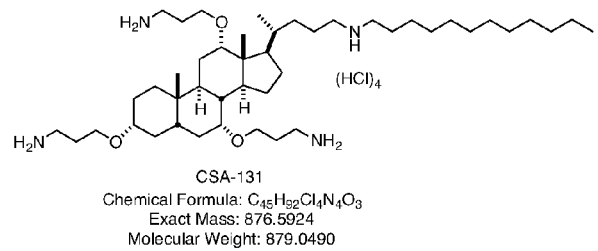

CSA-131
Chemical Formula: C₄₅H₉₂Cl₄N₄O₃
Exact Mass: 876.5924
Molecular Weight: 879.0490

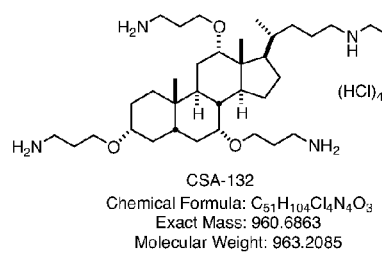

CSA-132
Chemical Formula: C₅₁H₁₀₄Cl₄N₄O₃
Exact Mass: 960.6863
Molecular Weight: 963.2085

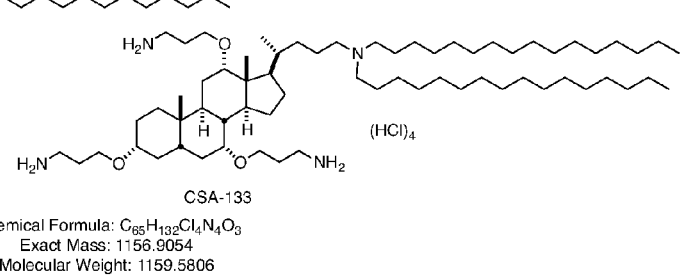

CSA-133
Chemical Formula: C₆₅H₁₃₂Cl₄N₄O₃
Exact Mass: 1156.9054
Molecular Weight: 1159.5806

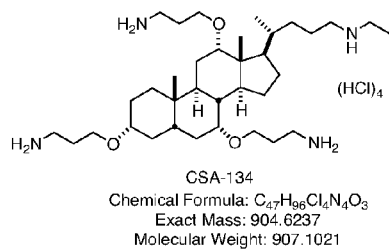

CSA-134
Chemical Formula: C₄₇H₉₆Cl₄N₄O₃
Exact Mass: 904.6237
Molecular Weight: 907.1021

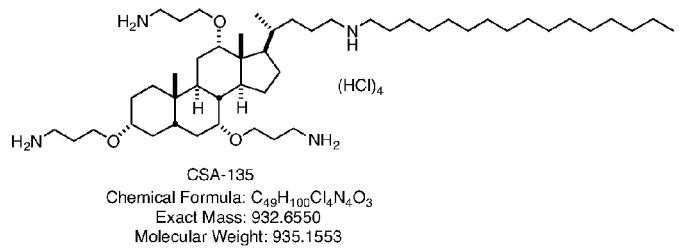

CSA-135
Chemical Formula: C₄₉H₁₀₀Cl₄N₄O₃
Exact Mass: 932.6550
Molecular Weight: 935.1553

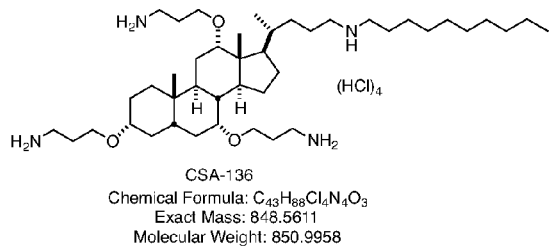

CSA-136
Chemical Formula: C₄₃H₈₈Cl₄N₄O₃
Exact Mass: 848.5611
Molecular Weight: 850.9958

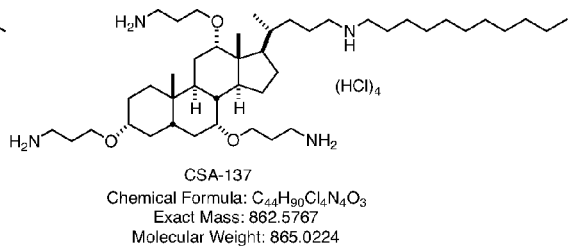

CSA-137
Chemical Formula: C₄₄H₉₀Cl₄N₄O₃
Exact Mass: 862.5767
Molecular Weight: 865.0224

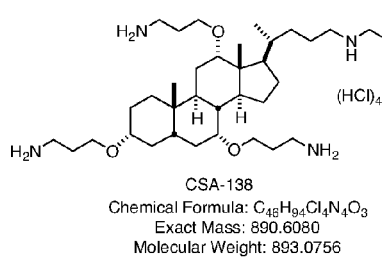

CSA-138
Chemical Formula: C₄₆H₉₄Cl₄N₄O₃
Exact Mass: 890.6080
Molecular Weight: 893.0756

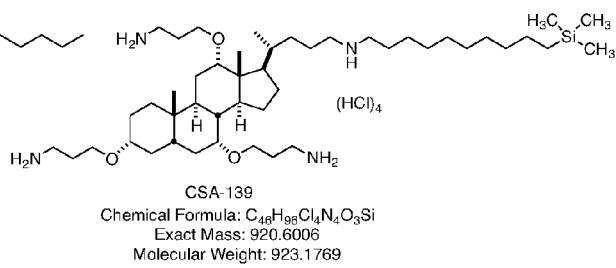

CSA-139
Chemical Formula: C₄₆H₉₆Cl₄N₄O₃Si
Exact Mass: 920.6006
Molecular Weight: 923.1769

FIG. 1 (Continued)

CSA-141

Chemical Formula: $C_{37}H_{66}Cl_3N_3O_8$
Exact Mass: 785.3915
Molecular Weight: 787.2942

CSA-142

Chemical Formula: $C_{39}H_{70}Cl_3N_3O_8$
Exact Mass: 813.4228
Molecular Weight: 815.3474

CSA-143

Chemical Formula: $C_{49}H_{90}Cl_3N_5O_{10}$
Exact Mass: 1013.5753
Molecular Weight: 1015.6254 ns caused by methicillin resistant *Staphylococcus aureus* ("MRSA").

MEDICAL DEVICES INCORPORATING CERAGENIN-CONTAINING COMPOSITES

CROSS-REFERENCE TO RELATED APPLICATIONS

This Application claims the benefit of U.S. Prov. App. Ser. No. 61/575,646, filed 25 Aug. 2011 and entitled "POLYMER RELEASED CATIONIC STEROIDAL ANTIMICROBIAL-13 FOR THE PREVENTION OF ORTHOPAEDIC DEVICE RELATED INFECTIONS" and U.S. Prov. Pat. App. Ser. No. 61/576,903, filed 16 Dec. 2011 entitled "MEDICAL DEVICES INCORPORATING CERAGENIN-CONTAINING COMPOSITES." This Application also cross-references U.S. Prov. Pat. App. Ser. No. 61/576,905, filed 16 Dec. 2011 and entitled "INCORPORATION OF PARTICULATE CERAGENINS IN POLYMERS." The above listed Applications are incorporated herein by reference in their entireties.

BACKGROUND

1. The Field of the Invention

The present invention relates to medical devices having a composite coating on at least a portion of the medical device.

2. The Relevant Technology

Surgical site infection ("SSI") (also referred to as postoperative infection or perioperative infection) is a major factor contributing to patient morbidity and mortality. A SSI is an infection that occurs after surgery in the part of the body where the surgery took place. Some of the common symptoms of SSI include: redness and pain around the surgical area, drainage of cloudy fluid from the surgical wound, and postoperative fever. SSIs contribute to longer hospital stays, longer rehabilitation times, greater antibiotic usage, higher patient expenses, and higher hospital expenses. In extreme cases, SSIs can lead to patient death.

Most patients who have surgery do not develop an infection. Nevertheless, some form of infection is associated with about 38% of surgical procedures. Between 5% and 50% of open fractures result in SSI and about 1-3% of elective procedures, which includes most joint replacement procedures, result in SSI. The organisms commonly associated with SSI include, but are not limited to, staphylococci and pseudomonads.

Doctors and hospitals employ a number of techniques to prevent SSI including, but not limited to, use of sterile technique and protective clothing, thorough cleaning of the surgical site prior to the procedure, and antibiotic prophylaxis (i.e., treatment with antibiotics prior to surgery). Antibiotic prophylaxis with standard antibiotics (e.g., penicillin and the like) is, however, controversial due to the fact that its effectiveness is questionable and it is believed that it may contribute to antibiotic resistance.

Even when sterile techniques are adhered to, surgical procedures can introduce bacteria and other microbes into the patient's body, which can colonize and infect different parts of the body. Antibiotics can be effective in treating such infections. However, once established in the patient's body, many SSIs can be resistant to antibiotic treatment. For example, many SSIs are associated with biofilm formation; biofilms are antibiotic-resistant aggregates of microorganisms in which cells adhere to each other on a surface. Many indwelling medical devices (e.g., catheters, replacement heart valves, joint replacement prostheses) are particularly susceptible to biofilm formation.

One technique that has been explored for preventing biofilm formation and other SSIs associated with these devices is to coat them with antibiotics. However, most antibiotics are readily soluble in water and their effectiveness can be diminished or eliminated if they are washed away or diluted. As a result, most antibiotics are generally not very effective for inhibiting microbial growth on surfaces. One technique that has been explored for making antibiotics more active on surfaces (e.g., polymer surfaces) is to covalently attach the antibiotic to the surface. For example, U.S. Pat. No. 7,854,941 to Urban et al. describes a system for covalently attaching antibiotics (e.g., β-lactam antibiotics) to reactive moieties that are themselves covalently attached to a polymer surface. By selecting appropriate antibiotics, growth of both Gram-negative and Gram-positive bacteria on the polymer surface can be inhibited by such a system.

SUMMARY

The present invention relates to implantable medical devices that have a ceragenin-containing composite material coated on at least a portion of the implantable body, wherein the composite comprises a polymeric material having ceragenin particles dispersed therethrough. The composites described herein that may be used to coat implantable medical devices have a high loading of ceragenin particles (e.g., about 10% to about 25%, by weight). As a result, the composites can be used to kill high concentrations of bacteria and other susceptible microbes over a sustained period of time.

In one embodiment, the implantable devices described herein can be fabricated by (i) providing an implantable body; (ii) providing a ceragenin mixture that includes ceragenin particles dispersed in a dispersant; (iii) dispersing the ceragenin mixture in the polymerizable material to form the polymerizable mixture; (iv) applying the polymerizable mixture to at least a portion of the implantable body to form a coating; and (v) polymerizing the polymerizable material to yield a composite coated on at least the portion of the implantable body, wherein the composite has the ceragenin particles dispersed therein. The ceragenin molecules are typically selected to be substantially insoluble in the polymerizable mixture.

These steps allow the ceragenin particles to be evenly distributed in the polymerizable material prior to polymerization, which in turn provides the composite with a regular void structure upon polymerization, wherein the void structure is created by the inclusion of the ceragenin particles in the polymeric material. Likewise, the dispersant can be used to adjust the viscosity of the polymerizable mixture in order to facilitate coating the implantable body with a composite having a selected thickness (e.g., at least one layer having a uniform thickness), and a regular void structure. In addition, composites described herein can tolerate the high ceragenin loading due, at least in part, to the small and/or uniform size of the ceragenin particles, which allows for a continuous polymer matrix surrounding the ceragenin particles to maintain mechanical stability of the polymeric material.

When water or other aqueous media comes into contact with the medical device with the composite coating, the water can dissolve or solublize all or a portion of the ceragenin compound from the composite over a sustained period of time (e.g., days or weeks). Due to the regular void structure, the ceragenin elutes at a characteristic elution over the sustained period of time and, preferably, essentially all of the ceragenin can be eluted from the composite. Importantly, the ceragenin compounds are only "activated" in the presence of water.

Once solublized, the ceragenin compound can inhibit microbial growth for an extended period of time. In one aspect, ceragenin molecules can elute out of the composite material and kill microbes that are in the vicinity of the composite. Alternatively, or in addition, microbes that migrate into the composite article come into contact with ceragenin molecules and are killed. The medical devices coated with the composites described herein have demonstrated efficacy for the prevention of and elimination of infections caused by Gram-positive, Gram-negative, and other antibiotic resistant bacteria. When applied to medical devices, the composites described herein have demonstrated the ability to eliminate and prevent surgical site implant-related infections caused by, for example, methicillin-resistant *Staphylococcus aureus* ("MRSA") in planktonic and biofilm forms.

In addition to the above, the ceragenin particles can be incorporated into the composite and remain stable during storage. Stability can be achieved by selecting ceragenins that are stable in the environment in which the composite is stored. The stability of the ceragenin compound can give the composite and any device coated with the composite a shelf life of weeks, months, or even years.

The stability of the ceragenin compounds can also be selected to facilitate manufacturing of the composite. For example, stable ceragenin compounds can be incorporated into a composite at a point during manufacturing prior to the article being exposed to high temperature, steam pressure, radiation, and/or oxidizing agents that would render other anti-microbial agents ineffective. Thus, the stability of the ceragenin compounds facilitates both the manufacture and use of the ceragenin compounds in composites.

The porous composites described herein can be used, for example, to coat at least a portion of a number of medical devices (e.g., bones plates, intramedullary devices, joint replacement prostheses, etc.) in order to prevent and/or treat post-operative infection.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Ceragenins

Ceragenin compounds, also referred to herein as cationic steroidal anti-microbial compounds (CSAs), are synthetically produced small molecule chemical compounds that include a sterol backbone having various charged groups (e.g., amine and cationic groups) attached to the backbone. The backbone can be used to orient the amine or guanidine groups on one face, or plane, of the sterol backbone. For example, a scheme showing a compound having primary amino groups on one face, or plane, of a backbone is shown below in Scheme I:

Scheme I

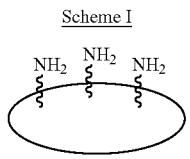

Ceragenins are cationic and amphiphilic, based upon the functional groups attached to the backbone. They are facially amphiphilic with a hydrophobic face and a polycationic face. Without wishing to be bound to any particular theory, the anti-microbial ceragenin compounds described herein act as anti-microbial agents (e.g., anti-bacterials, anti-fungals, and anti-virals). It is believed, for example, that the anti-microbial ceragenin compounds described herein act as anti-bacterials by binding to the cellular membrane of bacteria and other microbes and inserting into the cell membrane forming a pore that allows the leakage of ions and cytoplasmic materials that are critical to the microbe's survival and leading to the death of the affected microbe. In addition, the anti-microbial ceragenin compound described herein may also act to sensitize bacteria to other antibiotics. For example, at concentrations of the anti-microbial ceragenin compounds below the corresponding minimum bacteriostatic concentration, the ceragenins cause bacteria to become more susceptible to other antibiotics by increasing the permeability of the membrane of the bacteria.

The charged groups are responsible for disrupting the bacterial cellular membrane, and without the charged groups, the ceragenin compound cannot disrupt the membrane to cause cell death or sensitization. An example of a ceragenin compound is shown below at Formula I. As will be discussed in greater detail below, the R groups on Formula I can have a variety of different functionalities, thus providing the ceragenin compound with different properties.

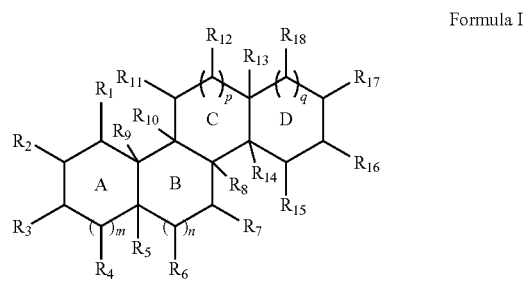

Formula I

Figure 1:
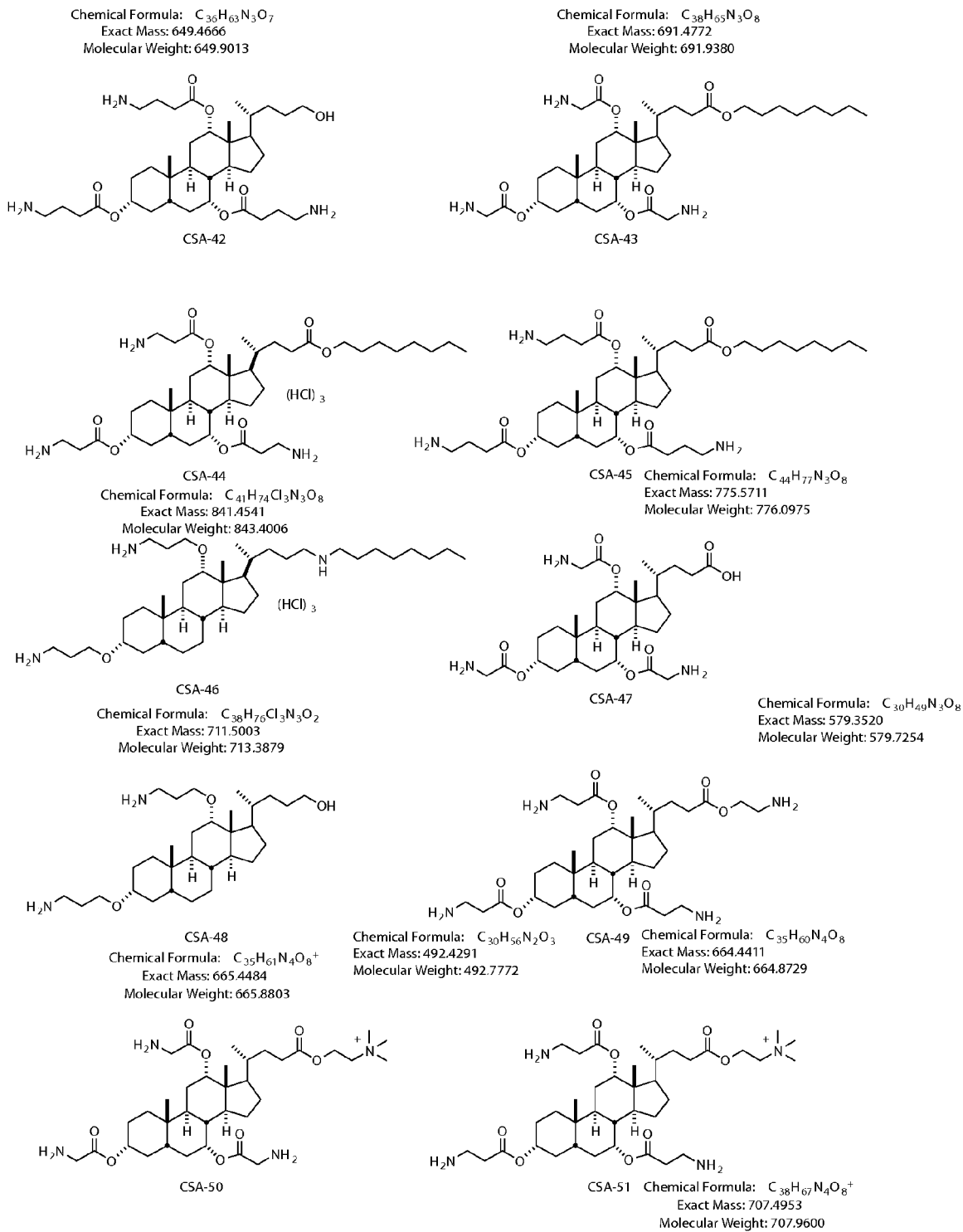
FIG. 1 illustrates example ceragenin compounds.
Figure 1:
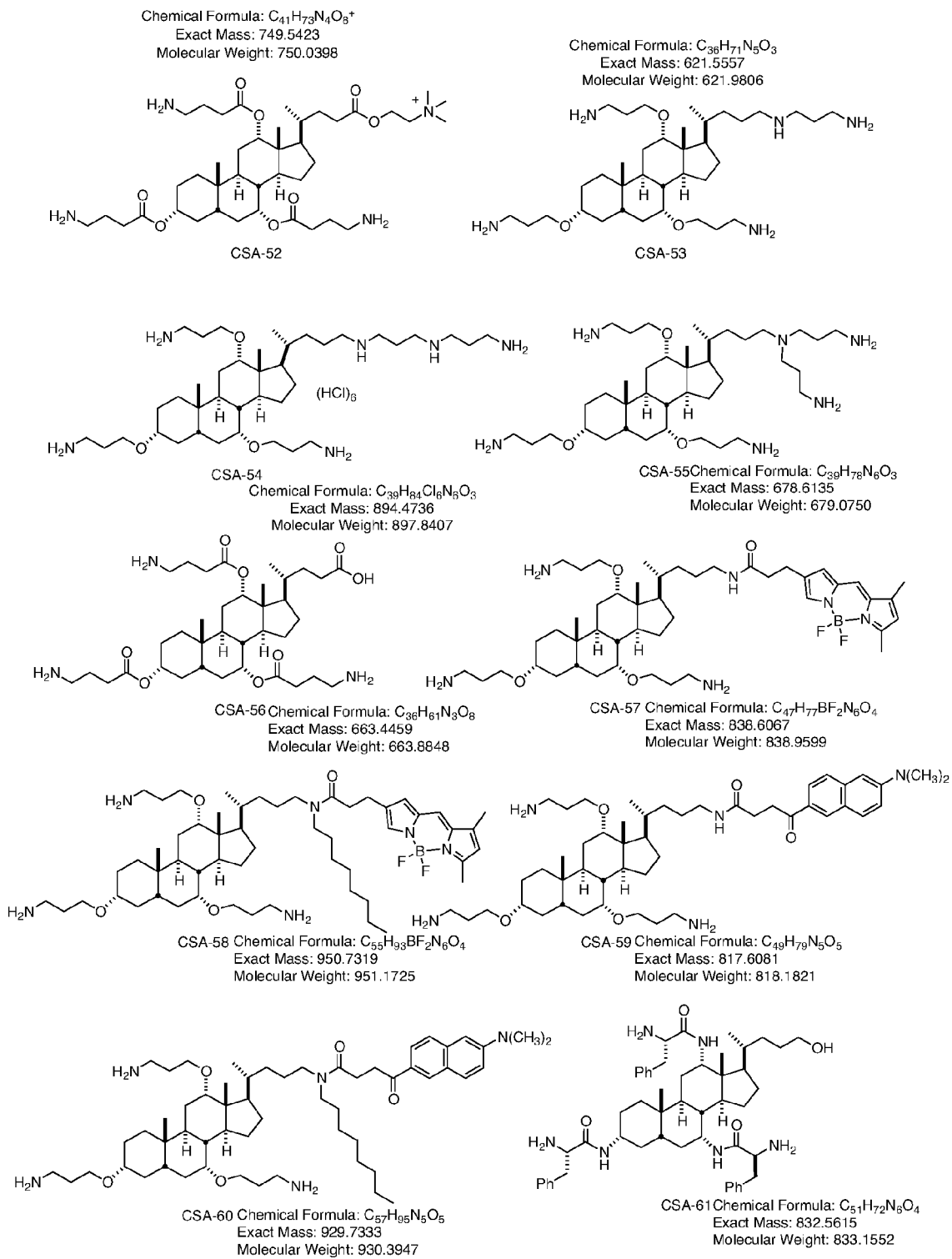
Figure 1:
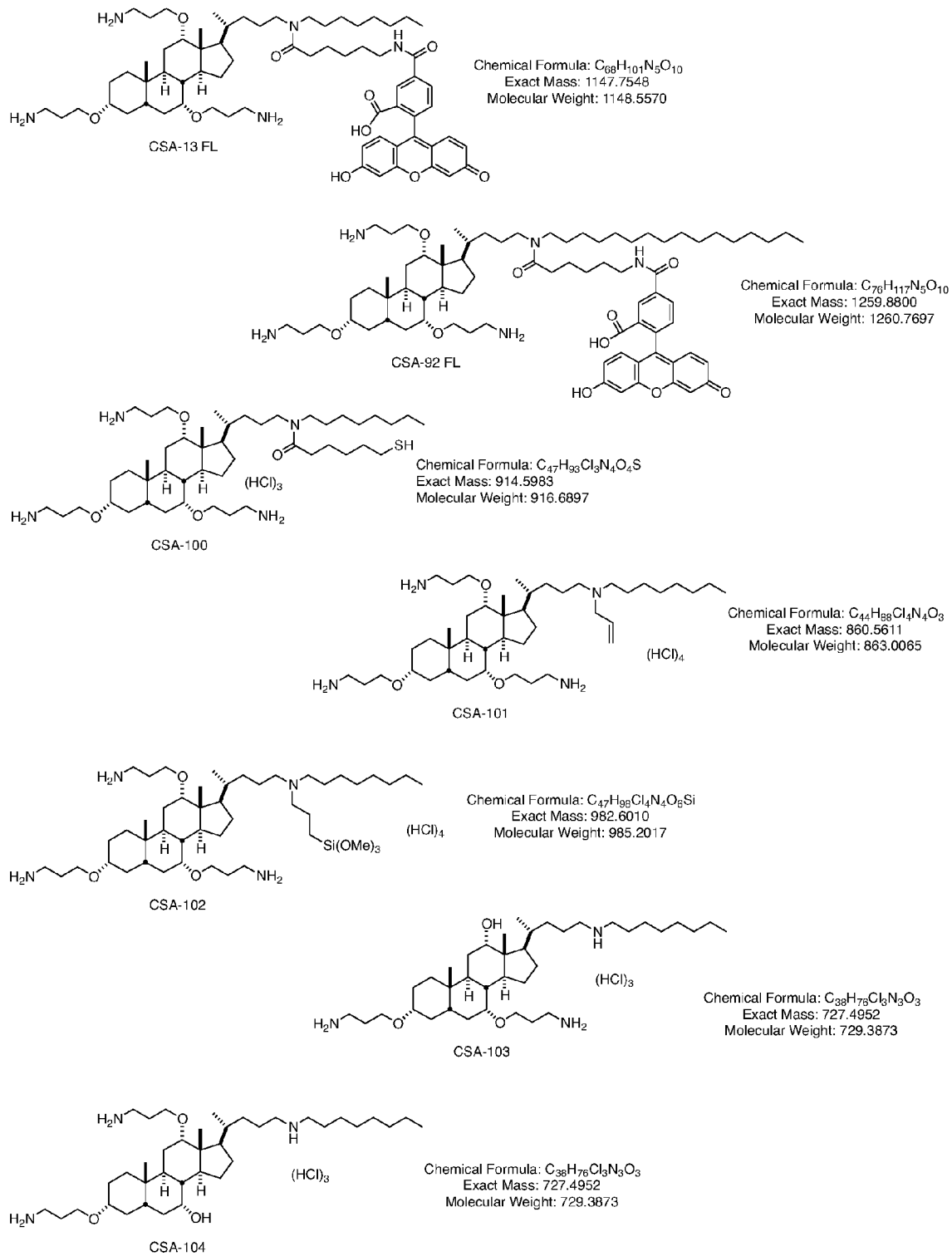
Figure 1:
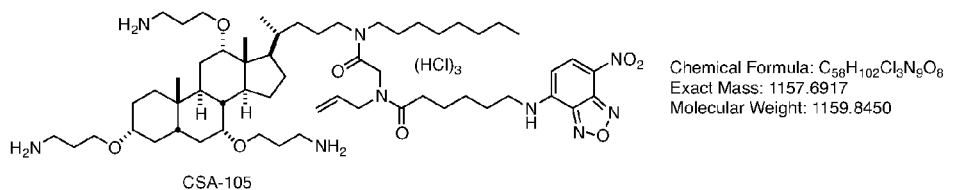
Figure 1:
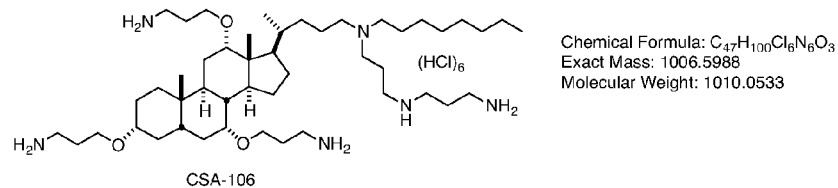
Figure 1:
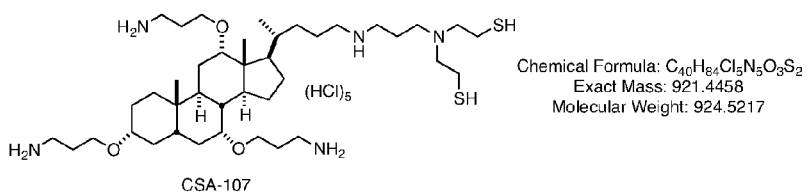
Figure 1:
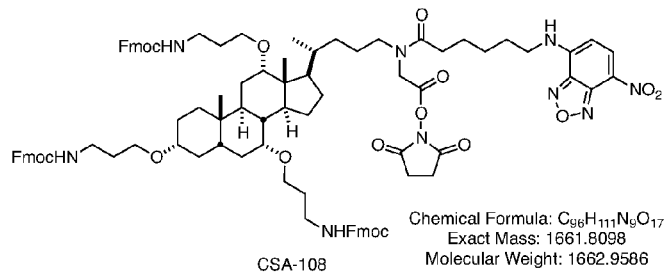
Figure 1:
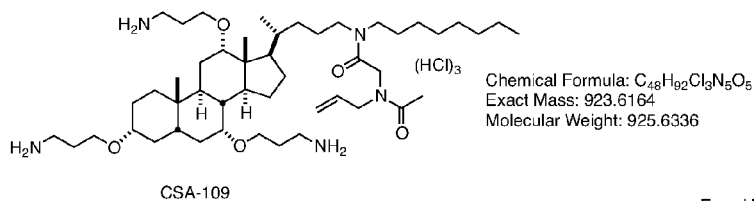
Figure 1:
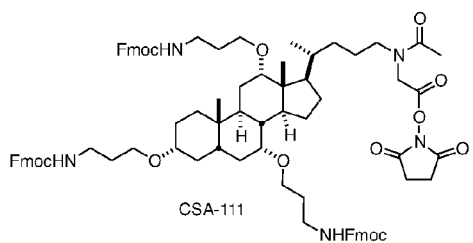
Figure 1:
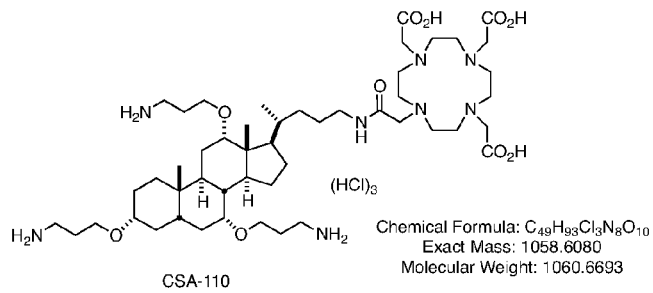
Figure 1:
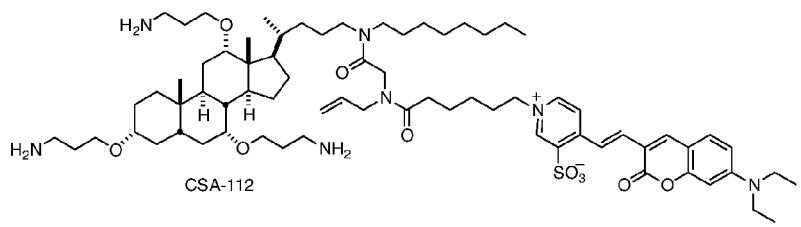
Figure 1:
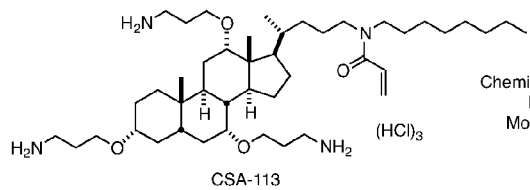
Figure 1:
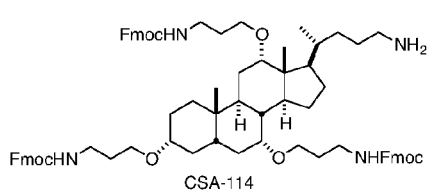
Figure 1:
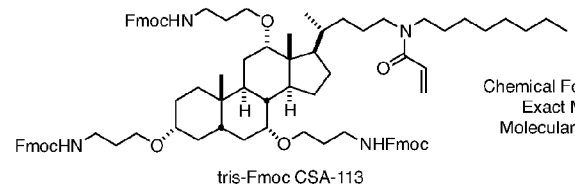
Figure 1:
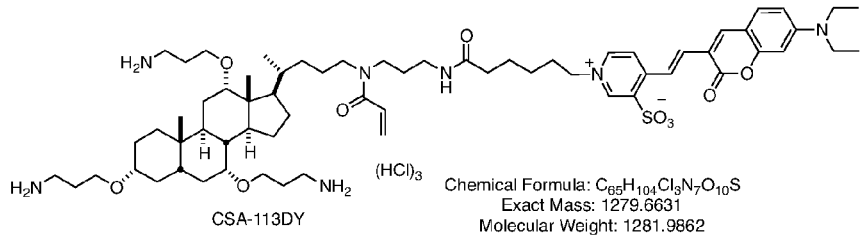
Figure 1:
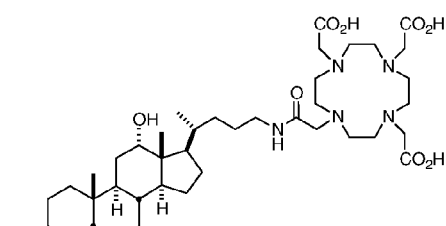
Figure 1:
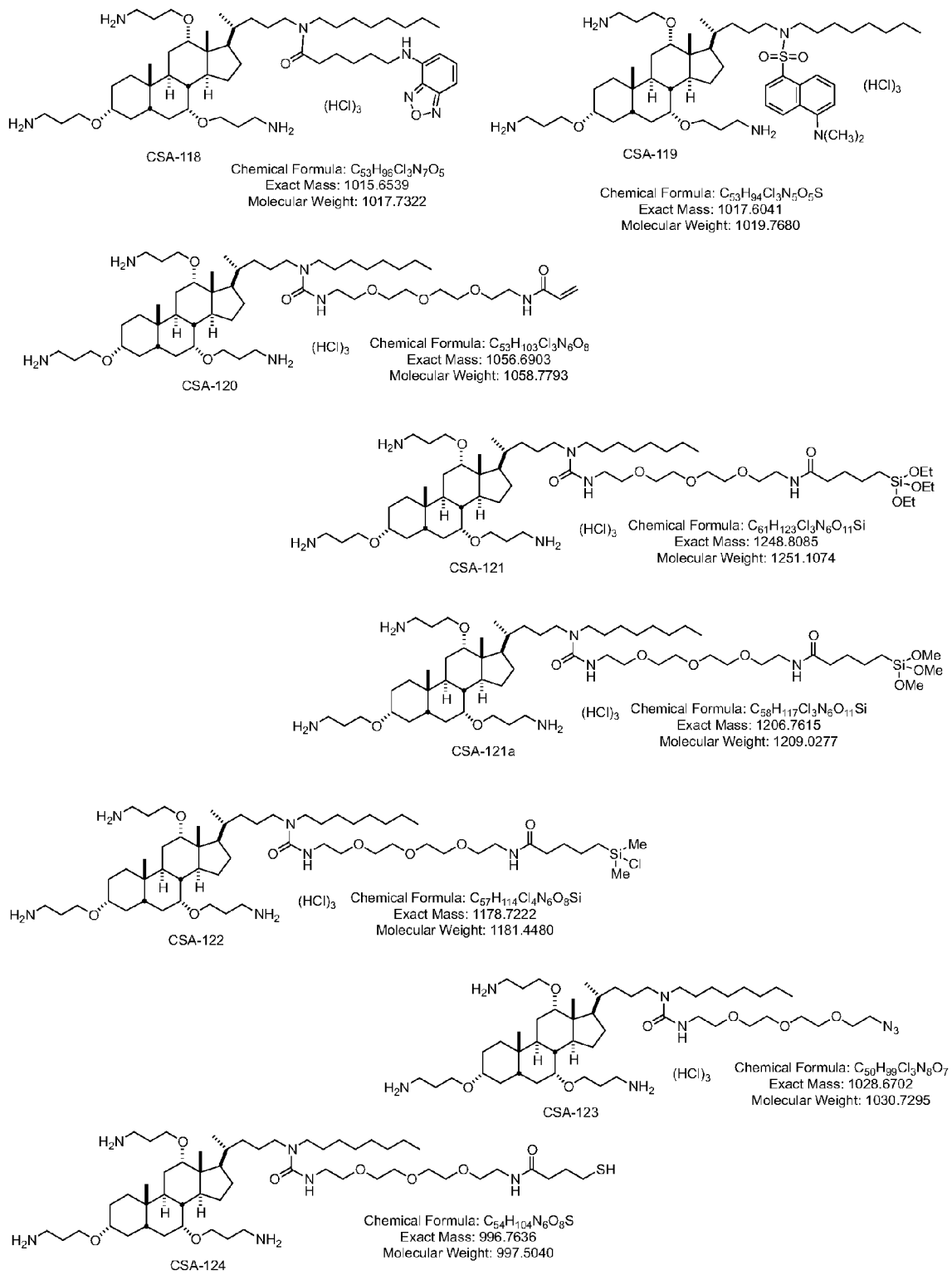
Figure 1:
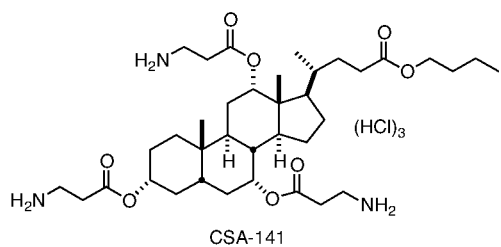
Figure 1:
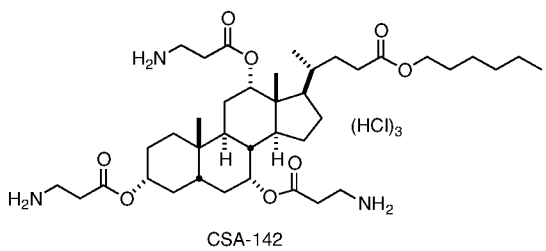
Figure 1:
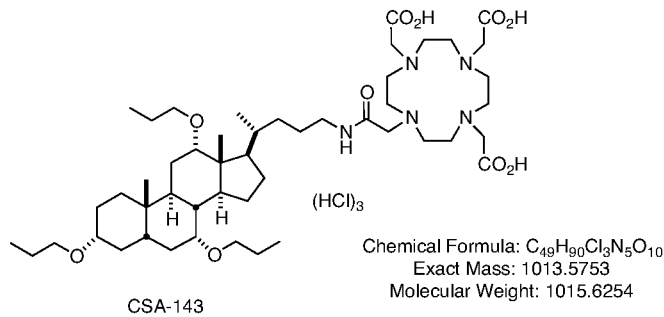

A number of examples of ceragenin compounds of Formula I that can be incorporated into the composite materials described herein are illustrated in FIG. 1.

Typically, ceragenins of Formula I are of two types: (1) ceragenins having cationic groups linked to the sterol backbone with hydrolysable linkages and (2) ceragenins having cationic groups linked to the sterol backbone with non-hydrolysable linkages.

Ceragenins of the first type can be "inactivated" by hydrolysis of the linkages coupling the cationic groups to the sterol backbone. For example, one type of hydrolysable linkage is an ester linkage. Esters are hydrolysed in the presence of water and base. Ceragenins of the first type are desirable, for example, where it is preferred that the ceragenins break down so that they do not buildup in the environment.

Ceragenins of the second type are not inactivated by hydrolysis. They are desired where long-term stability in an aqueous environment is preferred. Ceragenins of the second type are preferred for devices that need to be sterilized before use or otherwise exposed to elevated temperature and moisture, radiation, and oxidizing agents. In some embodiments, the ceragenin is selected to be stable after autoclaving, exposure to gamma radiation, or exposure to ethylene oxide. Likewise, the ceragenin used in the composites described herein may be selected to be shelf stable for days, weeks, months, or even years after the composite is prepared and/or sterilized.

A number of examples of compounds of Formula I that may be used in the embodiments described herein are illustrated in FIG. 1. Suitable examples of ceragenins include, but are not limited to, CSA-1-CSA-26, CSA-38-CSA-40, CSA-46, CSA-48, CSA-53-CSA-55, CSA-57-CSA-60, CSA-90-CSA-107, CSA-109, CSA-110, CSA-112, CSA-113, CSA-118-CSA-124, CSA-130-CSA-139, CSA-141, and CSA-142. In a preferred embodiment, the ceragenin is CSA-13.

II. Composite Materials

Figure 2:
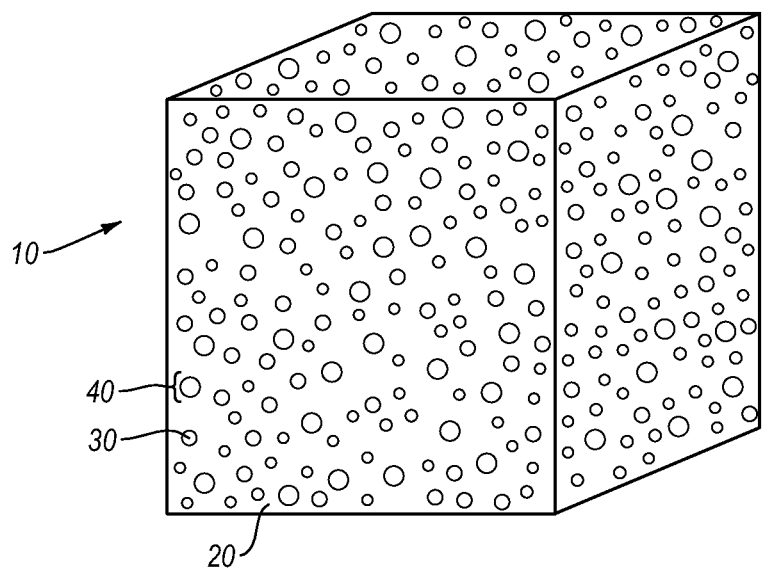
FIG. 2 illustrates a composite material according to one embodiment of the present invention.

A composite 10 according to one embodiment of the present invention is illustrated in FIG. 2. The composite 10 includes a polymer matrix 20 and a quantity of ceragenin particles 30 dispersed throughout the polymer matrix 20. The polymer matrix 20 can be fabricated from essentially any polymer material to provide a polymer structure into which the ceragenin particles 30 may be dispersed. The ceragenin particles 30 are dispersed in the polymer matrix 20 such that the ceragenin compounds may be eluted (i.e., dissolved) out of the ceragenin particles 30 and the composite 10 when water or other aqueous fluids are brought into fluid contact with the composite 10.

The particular material used for the polymer matrix 20 will depend on the composite 10 being manufactured. Suitable examples of polymers include, but are not limited to, silicones, vinyls, urethanes, methacrylates, polyesters, thermoplastics, thermoplastic alloys, co-polymers, and the like. Polymers can be provided as monomers, precursors, prepolymers, oligomers, or polymers. Such monomers, precursors, prepolymers, oligomers, or polymers can be polymerized and/or cross-linked using techniques well-known in the art to make the polymer matrix of the composites described herein.

In a specific embodiment, the composite 10 may be prepared by mixing ceragenin particles that are dispersed in a dispersant into a suspension that contains a solvent and polydimethylsiloxane ("PDMS") polymer chains. The PDMS polymer chains may be catalytically cross-linked to form the composite 10.

The polymer matrix 20 and the ceragenin particles 30 together define voids 40 in the composite. The voids 40 are essentially formed in the composite by the ceragenin particles 30. The ceragenin particles 30 dispersed in the composite 10 each comprise a cluster of ceragenin molecules and have an average particle and/or particle aggregate size in a range from 5 nanometers ("nm") to 40 micrometers ("μm"), 5 nm to 20 μm, 50 nm to 10 μm, 100 nm to 5 μm, or 1 μm to 10 μm. As a result, the voids 40 created by inclusion of the ceragenin particles have a size ranging from 5 nm to 40 μm, 5 nm to 20 μm, 50 nm to 10 μm, 100 nm to 5 μm, or 1 μm to 10 μm.

As a consequence of the small size of the ceragenin particles 30 and their regular dispersion in the composite 10, the polymer matrix 20 is able to form a more-or-less continuous polymer structure around each of the particles 30. This allows the composite 10 to have physical characteristics (e.g., hardness, tensile strength, elastomeric properties, etc.) that are similar to those that would be found in the polymer without the ceragenin particles 30 dispersed therein.

In one embodiment, the composite 10 can include up to 35% (weight/weight) ("wt %") of ceragenin particles 30. In another embodiment, the composite includes 1 wt % to 25 wt %, 16 wt % to 20 wt %, or 18 wt % ceragenin particles. It is believed that, because of the small size of the ceragenin particles 30, the composite 10 can include a large percentage of ceragenin particles 30 while maintaining the physical characteristics of the polymer matrix 20.

In one embodiment, the present invention may include a kit containing components that can be used to prepare a composite 10 as described herein. In one embodiment, the kit include ceragenin particles having an average particle and/or particle aggregate size in a range from 50 nm to 40 μm, a dispersant configured to disperse the ceragenin particles, a polymerizable material, and a protocol for preparing a composite that includes the ceragenin particles, the dispersant, and the polymerizable material.

In one embodiment, the present invention also includes a composite made from the kit, wherein the composite includes the ceragenin particles dispersed in a polymer made by polymerization of the polymerizable material, and wherein the composite includes 1 wt % to 25 wt %, 16 wt % to 20 wt %, or 18 wt % ceragenin particles.

III. Methods of Preparing a Composite Material

In one embodiment, a method of preparing a composite material is disclosed. The method includes (1) providing a mixture of ceragenin particles dispersed in a dispersant, (2) dispersing the mixture with a polymerizable material, and (3) polymerizing the polymerizable material to yield a composite material having the ceragenin particles dispersed therein.

Prior to dispersing the ceragenin particles in the dispersant, solid ceragenin material may be milled (i.e., ground) to produce particles having a suitable range of sizes. Substantially any milling method known in the art can be used. Suitable examples of milling techniques and devices include, but are not limited to, mortar and pestle, ball milling, rod milling, cut milling, jet milling, and the like. The milling can be carried out with a grinding aid and/or in a low moisture environment. Using a grinding apparatus such as a ball mill or jet mill ceragenins can be milled to a surprising small and uniform primary particle size, including average particle sizes ranging from 5 nm to 200 nm, 10 nm to 150 nm, 50 nm to 125 nm, 90 to 110 nm, or a range based on any combination of the lower and upper primary particle sizes recited in the foregoing ranges. Because ceragenins are relatively hygroscopic, some of the milled primary particles will tend to agglomerate to form larger agglomerated particles, yielding particle sizes ranging from 5 nm to 40 μm, 5 nm to 20 μm, 50 nm to 10 μm, 100 nm to 5 μm, 1 μm to 10 μm, or a range based on any combination of the lower and upper agglomerated particle sizes recited in the foregoing ranges. However, even though the ceragenin primary particles may tend to agglomerate in the presence of moisture, at least some percentage of the primary particles may not agglomerate. Thus, the solid ceragenin material may include a range of particle sizes in any combination of the lower and upper primary particle sizes recited in the foregoing ranges primary particle sizes and agglomerated particle sizes.

Prior to preparing the composite material, the milled particles may be placed into a dispersant capable of dispersing the ceragenin particles. Preferably, at least one ceragenin compound is substantially insoluble in the dispersant. For example, the dispersant can be a fluid that dissolves less than 40%, 20%, 10%, or 1% or even 0.1% of the mass of the ceragenins. Where the ceragenin particles are composed almost entirely of ceragenin compound, the ceragenin particles are substantially insoluble in the dispersant.

In one embodiment, the dispersant is a non-polar organic solvent. Suitable examples of non-polar organic solvents include, but are not limited to, naphtha, xylenes, pentane, cyclopentane, hexanes, cyclohexane, benzene, toluene, dioxane, chloroform, diethyl ether, dichloromethane, and combinations thereof.

Further to preparing the composite, a selected amount of the ceragenin particles in the dispersant is combined with a selected amount of a polymerizable material. For example, the ceragenin particles may be combined with the dispersant, and subsequently combined with the polymerizable material, such that the final composite material includes at least 1%, 5%, 10%, 15%, 20%, 25%, or 30% by weight of ceragenin particles and/or less than 35%, 30%, 25%, or 20% ceragenin particles or any range of the foregoing weight percentages.

In one embodiment, the dispersant is miscible or substantially miscible in the polymerizable material. Premixing the ceragenin particles with the dispersant allows the particles to be more evenly combined with the polymerizable material. Depending on the polymerizable material, it was found, for example, that the ceragenin particles would clump if they were mixed directly with the polymerizable material. In addition, the dispersant can be used to reduce the viscosity of the suspension containing the polymerizable material. This can be particularly advantageous for dispersing the ceragenin particles in situations where the polymerizable material is in a viscous solution. In one embodiment, the polymerizable material may also be dispersed in a dispersant, which may further facilitate dispersing the ceragenin particles in the polymerizable material. Also, as will be explained in greater detail below, controlling the viscosity of the solution prior to polymerization can facilitate applying layer(s) of the composite to a substrate.

Unless otherwise specified, the term "polymerizable material" includes materials having reactive groups that allow the material to be chain extended to form longer chain polymeric materials and/or to be cross-linked to form a cross-linked polymer. Examples of polymerizable materials include, but are not limited to, precursors (e.g., monomers, prepolymers, oligomers, or polymers) that can be polymerized and/or crosslinked to form a polymeric material. In addition, the polymerizable material may include solvents, dispersants, cross-linking agents, catalysts, and the like. The polymerizable material may be provided as a solid, a liquid, solution (i.e., a polymerizable compound dissolved in a solvent), a suspension (e.g., a colloidal suspension of a polymerizable compound and a solvent), a slurry, a dispersion, and the like.

In one embodiment, the polymerizable material is selected from the group consisting of a precursor of a silicone polymer, a vinyl polymer, a urethane polymer, a methacrylate polymer (e.g., an acrylic resin), a polyester, a thermoplastic, a thermoset polymer, a thermoplastic alloy, and combinations thereof. However, the particular material used for the polymerizable material will depend on the composite being manufactured. Such precursors can be polymerized and/or cross-linked using techniques well-known in the art to make the composites described herein.

The components of the polymerizable mixture can be selected to produce a particular viscosity to facilitate proper application of the composition to a surface and/or to form a material with a desired porosity. For example, viscosity can be adjusted by properly selecting the particular dispersant, the concentration and type of ceragenin, the particular polymerizable material, and the concentration of the ceragenin mixture in the polymerizable material. In some embodiments, the viscosity can have a lower range of 10 millipascal-seconds (mPa·s), 20 mPa·s, 50 mPa·s, 100 mPa·s, 500 mPa·s, 1000 mPa·s, 1500 mPa·s, 2000 mPa·s, 2500 mPa·s, 3000 mPa·s, 4000 mPa·s, or 5000 mPa·s, an upper range of 10,000 mPa·s, 9000 mPa·s, 8000 mPa·s, 7000 mPa·s, 6000 mPa·s, 5000 mPa·s, 4000 mPa·s, or 3000 mPa·s, or any combination of the above recited lower and upper viscosity ranges.

In one embodiment, the polymer used to form the composite materials described herein may have an intrinsic porosity; i.e., a porosity that is a property of the polymeric material itself. In addition, the intrinsic porosity can be adjusted using various techniques known in the art, such as, but not limited to, selecting the amount and type of various solvents in the polymerizable material (e.g., swelling of the polymerizable material in various solvents), introducing air into the polymerizable material, introducing porogens (e.g., micelles) into the polymerizable material, and the like. The porosity and/or the number and size of void spaces can also be selected by adjusting the concentration and type of ceragenin, the particle size of the ceragenin, the concentration and type of polymerizable material, and the concentration of the ceragenin mixture in the polymerizable material. In one embodiment, the percentage of void spaces created by the inclusion of the ceragenin particles (i.e., the "voids" or the "void structure") can be in a range from about 2% of surface area to about 50% of surface area, about 10% of surface area to about 30% of surface area, or about 15% of surface area to about 25% of surface area. The void structure may include pores having a size in a range from 5 nm to 20 μm.

In general, the greater the porosity, the more rapidly the ceragenin will elute out of the composite when the composite is brought into contact with water. However, percentage of void spaces created by the inclusion of the ceragenin particles and the elution rate of the ceragenin out of the composite are interconnected properties. That is, altering a property that affects void structure is also likely to affect the rate of elution. In addition, the intrinsic porosity of the polymeric material is also likely to affect the rate of elution. For example, the intrinsic porosity can provide pathways for water to access internal voids created by the ceragenin particles so that water can elute essentially all of the ceragenin out of the composite.

As such, in one embodiment, an elution rate of the ceragenin out of the composite can be selected by selecting the percentage of void spaces created by the inclusion of the ceragenin particles and/or the intrinsic porosity of the polymeric material. For example, if rapid elution is desired (e.g., 1-2 days), a composite having a high percentage of void spaces created by the inclusion of the ceragenin particles (e.g., about 30% or higher) can be made. If, on the other hand, longer term elution is desired (e.g., weeks to months), a composite having a low percentage of void spaces created by the inclusion of the ceragenin particles (e.g., about 10% or less) can be made. Likewise, multilayer composites can be made. If, for example, a rapid release followed by a slow release is desired, a composite having an outer layer having a high percentage of ceragenin particles and an inner layer having a lower percentage of ceragenin particles can be prepared. The reversing the order of the layers would yield a composite having a first slow release followed by a rapid release.

In one embodiment, the composite may be prepared by dispersing a mixture of ceragenin particles and a dispersant into a polymerizable material that includes a solvent and polydimethylsiloxane ("PDMS") polymer chains to form a polymerization mixture. In one embodiment, such PDMS polymer chains may be catalytically cross-linked to form the composite. The relative amounts of dispersant and PDMS may be adjusted to adjust the viscosity of the polymerization mixture in a desired range and to yield a composite having a desired concentration of ceragenin particulate (e.g. 16 wt % to 20 wt %).

In a specific embodiment, the composite may be prepared by dispersing a mixture of ceragenin particles dispersed in naphtha into a polymerizable material (e.g., MED-6607 RTV silicone available from NuSil Technology of Carpentaria, Calif.) to form a polymerization mixture. MED-6607 includes about 30 wt % PDMS pre-polymer suspended in naphtha. As-sold, MED-6607 includes the PDMS pre-polymer chains, a cross-linking agent, and a tin catalyst. The PDMS pre-polymer chains of MED-6607 in the polymerization mixture spontaneously cross-link in the presence of moisture to form the cross-linked composite having the ceragenin particles dispersed therethrough.

In order to characterize the MED-6607 polymer, a number of tests were performed on thin films containing ceragenin particles and on thin films having no ceragenin. Tensile testing was performed following ASTM standard D882-10. Results for n=15 thin films indicated that the tensile strength of silicone only was 2.26±0.58 MPa; silicone with CSA-13 at 18% w/w concentration was 0.90±0.33 MPa. Elongation testing showed that silicone only was 327.72%±75.68%; silicone with CSA-13 was 215.78%±39.01%. Elastic modulus testing with silicone only was 1.24±0.69 MPa, and with CSA-13 it was 3.20±1.39 MPa.

IV. Medical Devices

In one embodiment, the present invention includes a medical device. The medical device includes a body, and a composite material coated on at least a portion of the body, wherein the composite material comprises a polymeric material having ceragenin particles dispersed therethrough. A cross-sectional view of medical device 50 may be generally depicted in FIG. 3. The medical device 50 includes a body 60 having a layer 70 of a ceragenin-containing composite deposited thereon. The body 60 may be made from any suitable material. For example, the body 60 may be metal, ceramic, glass, paper, wood, polymeric (e.g., rubber or plastic), or a combination thereof. In one embodiment, the medical device 50 may be an implantable device. Suitable examples of implantable devices include, but are not limited to, at least a portion of a total joint replacement device, a bone plate, an osteointegrating implant, a spine repair or reconstruction device, a bone plug, a bone screw, an intramedullary rod, a shunt, a catheter, an endotracheal tube, a stent, a pacemaker, a pacemaker lead, and combinations thereof.

Figure 3:
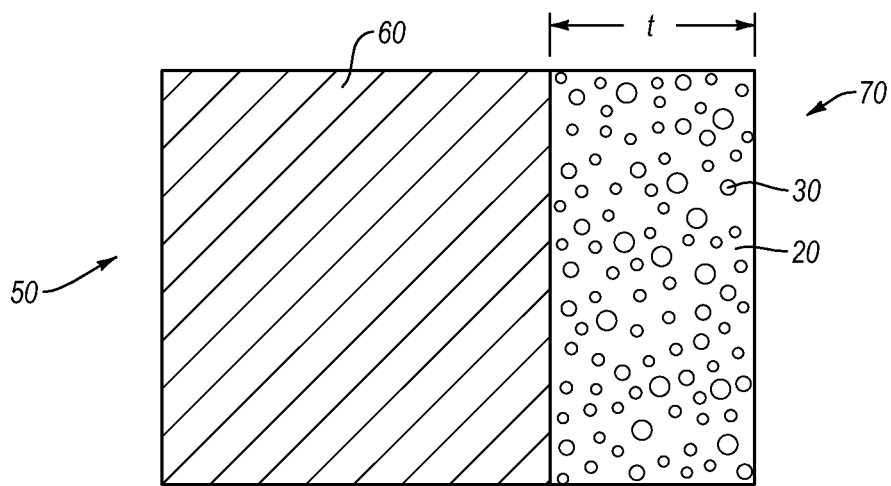
FIG. 3 is a cross-sectional view of a ceragenin-containing composite deposited on a substrate according to one embodiment of the present invention.

In FIG. 3, the layer 70 of the ceragenin-containing composite applied to the body 60 has a thickness "t." In one embodiment, the thickness of the layer 70 ranges from about 25 μm to about 500 μm, about 100 μm to about 400 μm, about 150 μm to about 300 μm, about 150 μm to about 250 μm, about 200 μm, or combination of the listed upper and lower thicknesses.

The medical device 50 may be placed into any suitable environment where it is desirable to kill bacteria or other susceptible microbes. When placed in an aqueous environment, the medical device 50 can reduce or eliminate bacteria and other susceptible microbes in the aqueous environment. Surprisingly, even where ceragenins elute too slowly to properly kill a microbial population, by placing the microbes in fluid contact with the medical device 50, microbes have been found to migrate into the polymer and be killed.

In one embodiment, the present invention includes a method of treating an infection. For example, the medical device 50 may be implanted into a body (e.g., a body of a human or another animal) at a site of a bone fracture or a joint replacement in order to prevent or treat a surgical site infection (i.e., a post-operative infection). The method includes (1) providing an implantable device at least a portion of which is coated with a composite material that includes ceragenin particles dispersed therethrough, (2) implanting the implantable device in a body, (3) eluting at least one ceragenin compound from the ceragenin particles into the body, and (4) killing one or more microbes in the body.

In one embodiment, the at least one ceragenin compound eluted from the ceragenin particles is sufficient to continue killing microbes for at least 1-15 days, at least 3-12 days, or at least 10 days after implanting the implantable device in the body.

To confirm that medical devices coated with the ceragenin-containing composites described herein are able to kill bacteria, various groups of titanium bone plugs were prepared. The titanium bone plugs were either uncoated, coated with MED-6607 ceragenin-containing silicone polymer prepared as described above, or with MED-6607 silicone polymer only. In the groups of bone plugs that were coated with ceragenin-containing silicone polymer, the silicone either contained 16 wt %, 18 wt %, or wt % ceragenin. Specifically, the groups of bone plugs were as follows:

0%—a titanium bone plug coated with silicone polymer with no ceragenin
16%—a titanium bone plug coated with silicone polymer containing 16% CSA-13 (w/w)
18%—a titanium bone plug coated with silicone polymer containing 18% CSA-13 (w/w)
18%—a titanium bone plug coated with silicone polymer containing 18% CSA-13 (w/w)
titanium—a titanium bone plug with no coating The bone plugs were placed into broth (e.g., 30 ml of broth) and challenged with ~5×10$^8$ colony forming units (CFU) of MRSA. In addition, a broth/MRSA-only control was prepared. Samples were withdrawn from each of the tubes at 0, 1, 2, 4, 8, 24, and 48 hours. The data for the 0, 1, 2, 4, 8, and 24 hour data points are graphed in FIG. 4.

Figure 4:
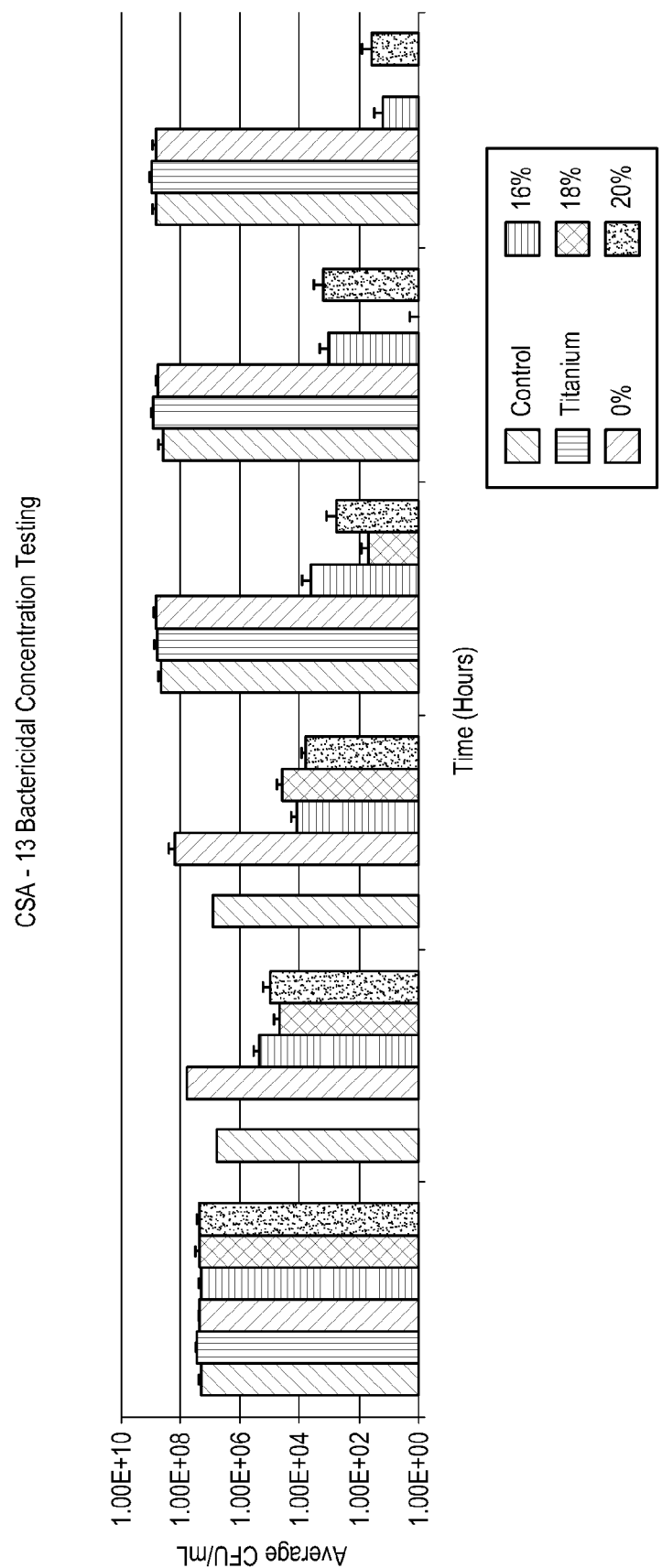
FIG. 4 is a graph showing numbers of viable planktonic (i.e., free-swimming) bacteria in a series of in vitro assays at various time points after being exposed to articles having a composite deposited on their surfaces with different concentrations of ceragenin compound in the composite.

As can be seen from the graph displayed in FIG. 4, numbers of viable bacteria (i.e., CFU/ml) went up in tubes where no CSA-13 was added (i.e., 0%, titanium, and control). In contrast, numbers of viable bacteria dropped dramatically in each of the tubes containing a bone plug with CSA-13 (i.e., 16%, 18%, and 20%). As between the tubes containing a bone plug with CSA-13, the bone plugs coated with the composite material containing 18% CSA-13 were clearly superior at the 4 and 8 hour time points. For example, there were essentially no viable bacterial in the 18% tubes. In contrast, the 16% tubes each contained about 1×10$^3$ CFU and the 20% tubes each contained about 5×10$^2$ CFU. By the 24 hour time point, the 20% had caught up to the 18, but the 16% still had considerable numbers of viable bacteria.

These results demonstrate that the ability of the composites described herein to deliver ceragenin is more than a function of loading the polymer with as much ceragenin as possible. Rather, the solubility of the ceragenin, the physical stability of the composite, including the intrinsic porosity of the polymeric material, and the void structure of the composite affect the elution of the ceragenin from the composite. The size and proximity of the voids created by the ceragenin particles and the intrinsic porosity of the polymeric material can have a significant effect on the diffusion of water through the composite, thus affecting the rate at which ceragenins can be eluted. For example, silicone polymers (e.g., MED-6607) have an intrinsic porosity with pores ranging from nanometer size to micrometer size. Other types of polymers (e.g., polyurethanes, acrylics, polyesters, polyethylenes, etc) may have more or less porosity as compared to silicone polymers.

Although the data illustrated in FIG. 4 are particular to the polymer MED-6607 and the ceragenin "CSA-13," those skilled in the art will recognize that similar elution profiles for ceragenins can be obtained for other types of polymers and ceragenins by following the teachings and procedures disclosed herein.

In similar sets of experiments, it was found that bone plugs coated with ceragenin-containing composites were superior to bone plugs coated with antibiotic-containing composites (vancomycin and linezolid). In addition, it was found that bone plugs coated with ceragenin-containing composites were able to kill bacteria in vivo when the bone plug was implanted in a sheep and the site of implantation was challenged with planktonic MRSA.

In one embodiment, the one or more microbes constitute a biofilm. Biofilms are aggregates of microorganisms in which cells adhere to each other on a surface. Biofilms can grow on inert and living surfaces such as, but not limited to, medical implants (e.g., joint prostheses, heart valves, bone plates, catheters, intrauterine devices, etc.), epithelial tissue, bone, and teeth (i.e., dental plaque). Biofilms are generally antibiotic-resistant and, once established in the body, they can be particularly difficult to eliminate with standard antibiotic treatment.

Figure 5:
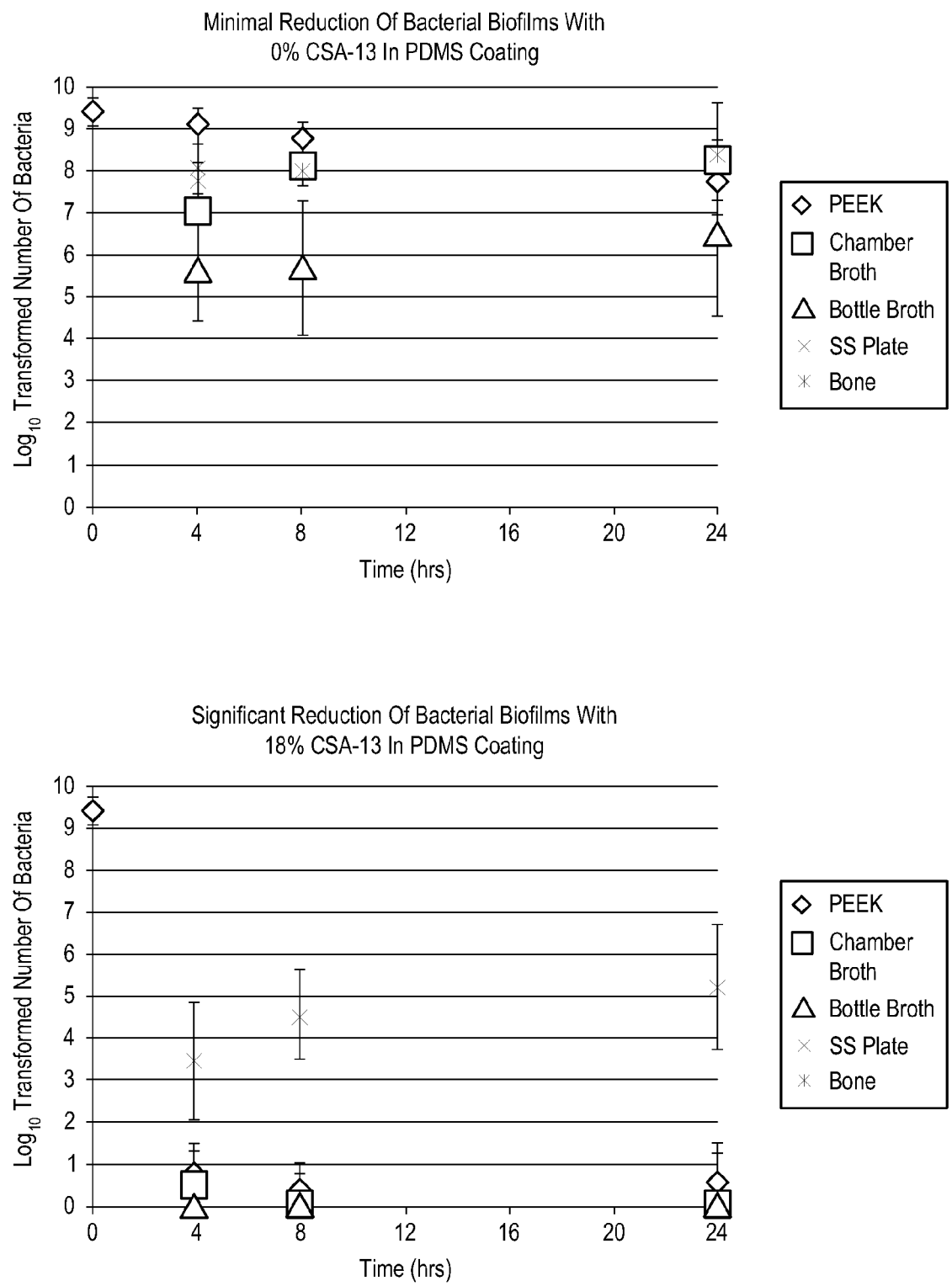
FIG. 5 is a graph showing numbers of viable biofilm-residing bacteria in a series of in vitro assays at various time points after being exposed to articles having a composite deposited on their surfaces with different concentrations of ceragenin compound in the composite.

In contrast to standard antibiotic treatment, the ceragenin-containing composite materials described herein have been shown to be particularly effective for elimination of biofilms. In one experiment, bone plates coated with ceragenin-containing composites were compared with bone plates coated with polymer only. Data relating to this experiment is illustrated in FIG. 5. Broth samples from polymer-only coated plates had an increase in the number of CFU/mL of broth at each time point collected and there was a minimal difference in the number of bacteria still residing in a biofilm on the surface of a material.

In contrast, results indicated that biofilms on the surface of a material that were placed in chambers with plates coated with ceragenin-containing composites (treatment group) had greater than an 8 $\log_{10}$ reduction of bacteria on the surface over a 24 hour period. That is, the broth samples collected from chambers that had plates coated with ceragenin-containing composites had no detectable amounts of bacteria after 24 hours. These results were surprising and unexpected.

Similar results were obtained in vivo when bone plates were coated with ceragenin-containing composites and were compared with bone plates coated with polymer only, then implanted into animals and challenged with biofilms. For example, in 100% of cases where animals were infected with biofilms and received bone plates coated with ceragenin-containing composites, the animals remained healthy and bacterial loads in and around the infection site were surprisingly and unexpectedly low (i.e., cell numbers were undetectable or below the limit of detection of between $10^0$ and $10^1$ cells). In contrast, 100% of animals who received polymer-only bone plates developed infection when they were infected with biofilms and bacterial loads in and around the infection site exceeded $10^6$ bacterial cells per gram of tissue, which is well above the standard for infection.

In addition, histological sections were compared from animals receiving bone plates. The animal groups were as follows: Group 1 (n=9)—Biofilm, PDMS only coated stainless steel ("SS") plates; Group 2 (n=9)—Biofilm, CSA-13 coated SS plates; Group 3 (n=9)—No biofilm, PDMS only coated SS plates; and Group 4 (n=8)—No biofilm, CSA-13 coated SS plates. The histological section displayed distinct morphologies of soft tissue and bone response to the various treatment methods. Foremost, seven sheep from Group 1 showed clinical signs of Grade III osteomyelitis that were confirmed by chronic inflammation, significant fibrous encapsulation near screws and plates, and necrotic bone with sequestra formation. Two sheep in Group 1 were euthanized after one week due to the severity of their infections. These sheep had not yet displayed significant signs of inflammation, necrotic bone or sequestra formation likely due to the shortness of time that they survived, but they had positive growth by culture and displayed significant clinical signs of Grade III infection. In contrast, none of the sheep in Group 2 or Group 4 showed signs of osteomyelitis and only one sheep in Group 3 had a soft tissue infection. These results were surprising and unexpected. And while inflammation was present in sheep from all groups, with the highest level of inflammation being present in Group 1 sheep, this is a normal response to surgical trauma.

Additional discussion of ceragenin-containing composites, their preparation, and in vitro and in vivo results associated with their use can be found in "In Vivo Efficacy of a Silicone—Cationic Steroid Antimicrobial Coating to Prevent Implant-Related Infection" by Dustin L. Williams et al., Biomaterials (in press) (expected publication 2012), the entirety of which is incorporated herein by reference.

V. Methods of Making an Implantable Device Coated with a Ceragenin-Containing Composite In one embodiment, the present invention includes a method for making an implantable body. The method includes (1) providing an implantable body, (2) applying a polymerizable mixture comprising a plurality of ceragenin particles dispersed in a polymerizable material to at least a portion of the implantable body to form a coating, and (3) polymerizing the polymerizable material to yield a composite coated on at least the portion of the implantable device, wherein the composite has the ceragenin particles dispersed therein. For example, the composite may include 1 wt % to 25 wt %, 16 wt % to 20 wt %, or 18 wt % ceragenin particles.

The polymerizable mixture may be coated onto a selected portion of a medical device by at least one of brush coating, dip coating, electrospray coating, or spin coating. If multiple coating layers are desired, the medical device may be coated more than once with a suitable amount of curing time between layers.

Suitable curing time between layers may be in a range from about 1 minute to 1 hour, 2 minutes to 30 minutes, 5 minutes to 20 minutes, 5 minutes to 15 minutes, 8 minutes to 12 minutes, or 10 minutes. For example, it was found that multiple layers of MED-6607 mixed with dispersant-suspended ceragenin particles at a ratio of 1:1 could be applied to a substrate (e.g., a medical device) with 10 minutes of curing between layers. Although these times are particular to the polymer MED-6607 and the ceragenin "CSA-13," those skilled in the art will recognize that similar curing times for multiple layer composite structures can be determined for other types of polymers and ceragenins by following the teachings and procedures disclosed herein.

In one embodiment, the thickness of the coating of the composite applied to the implantable body can be less than 500, 100, 50, or 10 μm and/or greater than 1, 5, 25, or 100 μm or any combination of the listed upper and lower ranges. In one embodiment, the ceragenin particles dispersed in the composite have an average particle size of less than 40, 30, 20, 10, 5, or 1 μm and/or greater than 10, 20, 50, 100, or 500 nm or any combination of the listed upper and lower ranges. As such, the thickness of the coating is at least 2.5, 5, 7.5, 10, 20, 50, or 100 times the average diameter of the particles.

In one embodiment, the method further includes (i) preparing a dispersion that includes the ceragenin particles and at least one dispersant selected from the group consisting of naphtha, xylenes, pentane, cyclopentane, hexanes, cyclohexane, benzene, toluene, dioxane, chloroform, diethyl ether, dichloromethane, and combinations, and (ii) dispersing the dispersion in the solution that includes the polymerizable material.

In one embodiment, the polymerizable material is provided in a solution that includes a polymerizable compound. In one embodiment the solution includes at least one solvent selected from the group consisting of naphtha, xylenes, pentane, cyclopentane, hexanes, cyclohexane, benzene, toluene, dioxane, chloroform, diethyl ether, dichloromethane, and combinations thereof.

In one embodiment, the solution further includes at least one dispersant selected from the group consisting of naphtha, xylenes, pentane, cyclopentane, hexanes, cyclohexane, benzene, toluene, dioxane, chloroform, diethyl ether, dichloromethane, and combinations thereof.

In one embodiment, the polymerizable material is selected from the group consisting of a precursor (i.e., a monomer, a prepolymer, an oligomer, or a polymer) of a silicone, a vinyl, a urethane, a methacrylate, a polyester, a thermoplastic, a thermoset polymer, a thermoplastic alloy, and combinations thereof. In a preferred embodiment, the composite comprises a silicone polymer.

In a specific example, a selected quantity of a dispersion of ceragenin particles in a dispersant is combined with a quantity of a solution that includes a polymerizable material (e.g., a cross-linkable PDMS polymer) suspended in a solvent. In one embodiment, the dispersant used to disperse the ceragenin particles and the solvent used to dissolve the polymerizable material are the same.

The amount of dispersant used to disperse the ceragenin particles and thus the amount added to the polymerizable material may be adjusted in order to adjust the viscosity of the mixture. The quantity of the ceragenin mixture dispersion that is added to the polymerizable material is selected to give a desired viscosity and a desired concentration of ceragenin particles in the composite.

In one embodiment, the method further includes sterilizing the implantable device with at least one of temperature and pressure (e.g., steam autoclaving), radiation (e.g., gamma radiation), or a chemical agent (e.g., ethylene oxide) after the polymerization. As discussed in greater detail elsewhere herein, the ceragenin compounds included in the composite are selected such that they are stable under such treatment. For example, thermogravimetric analysis has determined that the polymer/CSA-13 conjugate is stable to approximately 250° C.

VI. Ceragenin Compounds

The ceragenin compounds used to form the ceragenin particles discussed herein may have a structure as shown in Formula I:

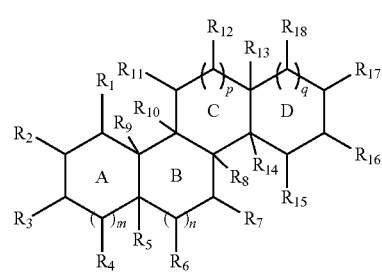

Formula I where each of fused rings A, B, C, and D is independently saturated, or is fully or partially unsaturated, provided that at least two of A, B, C, and D are saturated, wherein rings A, B, C, and D form a ring system; each of m, n, p, and q is independently 0 or 1; each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, ($C_1$-$C_{10}$) alkylcarboxy-($C_1$-$C_{10}$) alkyl, ($C_1$-$C_{10}$) alkylamino-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkyl, a substituted or unsubstituted aryl, a substituted or unsubstituted arylamino-($C_1$-$C_{10}$) alkyl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) amino alkyloxy-($C_1$-$C_{10}$) alkyl, a substituted or unsubstituted ($C_1$-$C_{10}$) aminoalkylcarboxy, a substituted or unsubstituted ($C_1$-$C_{10}$) aminoalkylaminocarbonyl, a substituted or unsubstituted ($C_1$-$C_{10}$) amino alkylcarboxamido, $H_2N$—$HC(Q_5)$—$C(O)$—$O$—, $H_2N$—$HC(Q_5)$—$C(O)$—$N(H)$—, ($C_1$-$C_{10}$) azidoalkyloxy, ($C_1$-$C_{10}$) cyanoalkyloxy, P.G.-HN—$HC(Q_5)$-$C(O)$—$O$—, ($C_1$-$C_{10}$) guanidinoalkyloxy, ($C_1$-$C_{10}$) quaternaryammoniumalkylcarboxy, and ($C_1$-$C_{10}$) guanidinoalkyl carboxy, where $Q_5$ is a side chain of any amino acid (including a side chain of glycine, i.e., H), P.G. is an amino protecting group, and each of $R_5$, $R_8$, $R_9$, $R_{10}$, $R_{13}$, and $R_{14}$ is independently deleted when one of fused rings A, B, C, or D is unsaturated so as to complete the valency of the carbon atom at that site, or selected from the group consisting of hydrogen, hydroxyl, a substituted or unsubstituted ($C_1$-$C_{10}$) alkyl, ($C_1$-$C_{10}$) hydroxyalkyl, ($C_1$-$C_{10}$) alkyloxy-($C_1$-$C_{10}$) alkyl, a substituted or unsubstituted ($C_1$-$C_{10}$) aminoalkyl, a substituted or unsubstituted aryl, ($C_1$-$C_{10}$) haloalkyl, $C_2$-$C_6$ alkenyl, $C_2$-$C_6$ alkynyl, oxo, a linking group attached to a second steroid, a substituted or unsubstituted ($C_1$-$C_{10}$) aminoalkyloxy, a substituted or unsubstituted ($C_1$-$C_{10}$) aminoalkylcarboxy, a substituted or unsubstituted ($C_1$-$C_{10}$) aminoalkylaminocarbonyl, $H_2N$—$HC(Q_5)$-$C(O)$—$O$—, $H_2N$—$HC(Q_5)$-$C(O)$—$N(H)$—, ($C_1$-$C_{10}$) azidoalkyloxy, ($C_1$-$C_{10}$) cyanoalkyloxy, P.G.-HN—$HC(Q_5)$-$C(O)$—$O$—, ($C_1$-$C_{10}$) guanidinoalkyloxy, and ($C_1$-$C_{10}$) guanidinoalkylcarboxy, where $Q_5$ is a side chain of any amino acid, PG. is an amino protecting group, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of a substituted or unsubstituted ($C_1$-$C_{10}$) aminoalkyl, a substituted or unsubstituted ($C_1$-$C_{10}$) aminoalkyloxy, ($C_1$-$C_{10}$) alkylcarboxy-($C_1$-$C_{10}$) alkyl, ($C_1$-$C_{10}$) alkylamino-($C_1$-$C_{10}$) alkylamino, ($C_1$-$C_{10}$) alkylamino-($C_1$-$C_{10}$) alkylamino-($C_1$-$C_{10}$) alkylamino, a substituted or unsubstituted ($C_1$-$C_{10}$) aminoalkylcarboxy, a substituted or unsubstituted arylamino($C_1$-$C_{10}$) alkyl, a substituted or unsubstituted ($C_1$-$C_{10}$)

aminoalkyloxy-($C_1$-$C_{10}$) aminoalkylaminocarbonyl, a substituted or unsubstituted ($C_1$-$C_{10}$) aminoalkylaminocarbonyl, a substituted or unsubstituted ($C_1$-$C_5$) aminoalkylcarboxyamido, a ($C_1$-$C_{10}$) quaternaryammonium alkylcarboxy, $H_2N$—HC($Q_5$)-C(O)—O—, $H_2N$—HC($Q_5$)-C(O)—N(H)—, ($C_1$-$C_{10}$) azidoalkyloxy, ($C_1$-$C_{10}$) cyanoalkyloxy, P.G.-HN—HC($Q_5$)-C(O)—O—, ($C_1$-$C_{10}$) guanidinoalkyloxy, and a ($C_1$-$C_{10}$) guanidinoalkylcarboxy; or a pharmaceutically acceptable salt thereof.

In Formula I, at least two or three of $R_3$, $R_7$, or $R_{12}$ may independently include a cationic moiety attached to the Formula I structure via a non-hydrolysable or hydrolysable linkage. For the embodiments discussed herein, the linkage is preferably non-hydrolysable under conditions of sterilization and storage, and physiological conditions. Optionally, a tail moiety may be attached to Formula I at $R_{17}$. The tail moiety may be charged, uncharged, polar, non-polar, hydrophobic, amphipathic, and the like. Although not required, at least two or three of m, n, p. and q are 1. In a preferred embodiment, m, n, and p=1 and q=0.

A "ring" as used herein can be heterocyclic or carbocyclic. The term "saturated" used herein refers to the fused ring of Formula I having each atom in the fused ring either hydrogenated or substituted such that the valency of each atom is filled. The term "unsaturated" used herein refers to the fused ring of Formula I where the valency of each atom of the fused ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$; $R_8$ and $R_{10}$; and $R_{13}$ and $R_{14}$.

The term "unsubstituted" used herein refers to a moiety having each atom hydrogenated such that the valency of each atom is filled.

The term "halo" used herein refers to a halogen atom such as fluorine, chlorine, bromine, or iodine.

Examples of amino acid side chains include but are not limited to H (glycine), methyl(alanine), —$CH_2$—(C=O)—$NH_2$(asparagine), —$CH_2$—SH (cysteine), and —CH(OH)—$CH_3$ (threonine).

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, CI, Br, and I), hydroxyl, protected hydroxyl, amino, protected amino, carboxy, protected carboxy, cyano, methylsulfonylamino, alkoxy, acyloxy, nitro, and lower haloalkyl.

The term "substituted" used herein refers to moieties having one, two, three or more substituents, which may be the same or different, each replacing a hydrogen atom. Examples of substituents include but are not limited to halogen (e.g., F, CI, Br, and I), hydroxyl, protected hydroxyl, amino, protected amino, carboxy, protected carboxy, cyano, methylsulfonylamino, alkoxy, alkyl, aryl, aralkyl, acyloxy, nitro, and lower haloalkyl.

An aryl group is a $C_{6-20}$ aromatic ring, wherein the ring is made of carbon atoms (e.g., $C_6$-$C_{14}$, $C_{6-10}$ aryl groups). Examples of haloalkyl include fluoromethyl, dichloromethyl, trifluoromethyl, 1,1-difluoroethyl, and 2,2-dibromoethyl.

An aralkyl group is a group containing 6-20 carbon atoms that has at least one aryl ring and at least one alkyl or alkylene chain connected to that ring. An example of an aralkyl group is a benzyl group.

A linking group is any divalent moiety used to link one compound to another. For example, a linking group may link a second compound to a compound of Formula I. An example of a linking group is ($C_1$-$C_{10}$) alkyloxy-($C_1$-$C_{10}$) alkyl.

Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure. Further examples and conditions are found in T. W. Greene, *Protective Groups in Organic Chemistry*, (1st ed., 1981, 2nd ed., 1991).

A person of skill will recognize that various ceragenin compounds described herein preserve certain stereochemical and electronic characteristics found in steroids. The term "single face," as used herein, refers to substituents on the fused sterol backbone having the same stereochemical orientation such that they project from one side of the molecule. For example, substituents bound at $R_3$, $R_7$ and $R_{12}$ of Formula I may be all β-substituted or α-substituted. The configuration of the moieties $R_3$, $R_7$ and $R_{12}$ may be important for interaction with the cellular membrane.

Compounds include but are not limited to compounds having cationic groups (e.g., amine or guanidine groups) covalently attached to a steroid backbone or scaffold at any carbon position, e.g., cholic acid. In various embodiments, a group is covalently attached at anyone, or more, of positions $R_3$, $R_7$, and $R_{12}$ of the sterol backbone. In additional embodiments, a group is absent from anyone, or more, of positions $R_3$, $R_7$, and $R_{12}$ of the sterol backbone.

Anti-microbial CSA compounds described herein may also include a tether or "tail moiety" attached to the sterol backbone. The tail moiety may have variable chain length or size and may be one of charged, uncharged, polar, non-polar, hydrophobic, amphipathic, and the like. In various embodiments, a tail moiety may be attached at $R_{17}$ of Formula I. A tail moiety may include the heteroatom (O or N) covalently coupled to the sterol backbone. The tail moiety may, for example, be configured to alter the hydrophobicity/hydrophilicity of the ceragenin compound. Ceragenin compounds of the present disclosure having different degrees of hydrophobicity/hydrophilicity may, for example, have different rates of uptake into different target microbes. Likewise, altering the hydrophobicity/hydrophilicity of the ceragenin compounds described herein may affect the retention of the ceragenin compounds in certain media.

Other ring systems can also be used, e.g., 5-member fused rings. Compounds with backbones having a combination of 5- and 6-membered rings are also contemplated. Cationic functional groups (e.g., amine or guanidine groups) can be separated from the backbone by at least one, two, three, four or more atoms.

Additional embodiments of the invention are described in Exhibits A and B attached hereto and can be used alone or in combination with any of the embodiments described herein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A medical device, comprising
an implantable body; and
a composite coated on at least a portion of the implantable body, the composite comprising a polymeric material having ceragenin particles comprised of at least one type of ceragenin compound dispersed therein,
wherein the ceragenin particles each comprise a cluster of ceragenin molecules,
wherein the ceragenin particles are disposed in a void structure in the polymeric material,
wherein the ceragenin particles comprise 1 wt % to 25 wt % of the composite.

2. The medical device of claim 1, wherein the polymeric material is selected from the group consisting of a silicone polymer, a vinyl polymer, a urethane polymer, a methacrylate polymer, a polyester, and combinations thereof.

3. The medical device of claim 1, wherein the composite coated on at least the portion of the implantable body has a thickness less than 500 µm and greater than 1 µm.

4. The medical device of claim 1, wherein the composite includes 16 wt % to 20 wt % ceragenin particles.

5. The medical device of claim 1, wherein the ceragenin particles have an average particle size in a range from 5 nanometers ("nm") to 20 micrometers ("µm").

6. The medical device of claim 1, wherein the void structure is formed by the ceragenin particles.

7. The medical device of claim 6, wherein the void structure includes pores having a size in a range from 5 nm to 20 µm.

8. The medical device of claim 1, wherein the composite coated on at least a portion of the implantable body is configured to elute at least one ceragenin molecule when the implantable body contacts an aqueous environment.

9. The medical device of claim 1 formed according to a method comprising:
providing the implantable body;
providing a ceragenin mixture that includes the ceragenin particles dispersed in a dispersant;
dispersing the ceragenin mixture in a polymerizable material to form a polymerizable mixture;
applying the polymerizable mixture to at least a portion of the implantable body to form a coating; and
polymerizing the polymerizable material to yield the composite coated on at least the portion of the implantable body.

10. The medical device of claim 9, wherein the applying includes at least one of brush coating, dip coating, electrospray coating, spin coating, melt spinning, or electro spinning.

11. The medical device of claim 9, wherein the polymerizable mixture has a viscosity in a range from about 500 mPa·s to about 6000 mPa·s.

12. The medical device of claim 9, wherein the polymerizable mixture has a viscosity in a range from about 10 mPa·s to about 10,000 mPa·s so as to be suitable for at least one of brush coating, dip coating, electrospray coating, spin coating, melt spinning, or electro spinning.

13. The medical device of claim 9, wherein the composite coated on at least the portion of the implantable body has a thickness that is at least 2.5 to 100 times greater than an average diameter of the plurality of ceragenin particles.

14. The medical device of claim 9, wherein the dispersant is selected from the group consisting of naphtha, xylenes, pentane, cyclopentane, hexanes, cyclohexane, benzene, toluene, dioxane, chloroform, diethyl ether, dichloromethane, and combinations thereof.

15. The medical device of claim 9, the method further comprising sterilizing the implantable body with at least one of temperature, pressure, radiation, or a chemical agent after polymerizing the polymerizable material to yield the composite.

16. The medical device of claim 9, wherein the polymerizable material is selected from the group consisting of a precursor of a silicone polymer, a vinyl polymer, a urethane polymer, a methacrylate polymer, a polyester, and combinations thereof.

17. A method of treating an infection, comprising:
providing a medical device as in claim 1;
implanting the implantable body in an animal body;
eluting at least one ceragenin compound from the ceragenin particles into the animal body; and
killing one or more microbes in the animal body.

18. The method of claim 17, wherein the one or more microbes comprise a biofilm.

19. The method of claim 17, wherein the at least one ceragenin compound eluted from the ceragenin particles is sufficient to continue killing microbes for at least 1-15 days after implanting the implantable device in the body.

20. The method of claim 17, wherein the animal body is a human body.

21. A medical device, comprising
an implantable body; and
a composite coated on at least a portion of the implantable body, the composite comprising a polymeric material having ceragenin particles comprised of at least one type of ceragenin compound dispersed therein,
wherein the ceragenin particles each comprise a cluster of ceragenin molecules,
wherein the ceragenin particles are disposed in a void structure in the polymeric material,
wherein the void structure is selected so as to assist elution of ceragenin molecules from the composite during use; and
wherein the ceragenin particles comprise up to 35 wt % of the composite.

* * * * *

UNITED STATES PATENT AND TRADEMARK OFFICE
CERTIFICATE OF CORRECTION

PATENT NO.         : 8,945,217 B2                                        Page 1 of 1
APPLICATION NO.    : 13/594612
DATED              : February 3, 2015
INVENTOR(S)        : Savage et al.

It is certified that error appears in the above-identified patent and that said Letters Patent is hereby corrected as shown below:

Title Page (57)
Abstract, Line 6, change "5 Ξm" to --5μm--

Specification

Column 9
Line 2, change "The reversing the order" to --The reversing of the order--

Column 15
Line 51, change "CI to --Cl--
Line 60, change "CI to --Cl--

Signed and Sealed this
Twenty-ninth Day of March, 2016

Michelle K. Lee
*Director of the United States Patent and Trademark Office*